(12) United States Patent
Yoshino

(10) Patent No.: US 8,420,212 B2
(45) Date of Patent: Apr. 16, 2013

(54) SILANE COUPLING AGENTS WITH HEAT RESISTANCE, DURABILITY, RELEASABILITY AND ANTIFOULING PROPERTY, AND PROCESS FOR PRODUCING THESE COMPOUNDS

(75) Inventor: Norio Yoshino, Tokyo (JP)

(73) Assignee: Tokyo University of Science Educational Foundation Administrative Organization, Tokyo (JP)

(*) Notice: Subject to any disclaimer, the term of this patent is extended or adjusted under 35 U.S.C. 154(b) by 646 days.

(21) Appl. No.: 12/529,772

(22) PCT Filed: Mar. 6, 2008

(86) PCT No.: PCT/JP2008/054074
§ 371 (c)(1),
(2), (4) Date: Sep. 28, 2009

(87) PCT Pub. No.: WO2008/108438
PCT Pub. Date: Sep. 12, 2008

(65) Prior Publication Data
US 2010/0119848 A1 May 13, 2010

(30) Foreign Application Priority Data
Mar. 6, 2007 (JP) .................. 2007-055975

(51) Int. Cl.
*B32B 17/06* (2006.01)
*B32B 15/04* (2006.01)
*C07F 7/18* (2006.01)

(52) U.S. Cl.
USPC ........ 428/333; 252/182.2; 428/429; 428/447; 556/470; 556/485

(58) Field of Classification Search ............... 252/182.2; 428/333, 429, 447; 556/470, 485
See application file for complete search history.

(56) References Cited

FOREIGN PATENT DOCUMENTS

| JP | 09-315923 | 12/1997 |
|---|---|---|
| JP | 10-265242 | 10/1998 |
| JP | 2000-169483 | 6/2000 |
| JP | 2000-342602 | 12/2000 |
| JP | 2004-107274 | 4/2004 |
| JP | 2007-238567 | 9/2007 |
| JP | 2008-063594 | 3/2008 |
| JP | 2008-266313 | 11/2008 |
| JP | 2009-132637 | 6/2009 |

OTHER PUBLICATIONS

Yoshino et al., Synthesis of novel highly heat-resistant fluorinated silane coupling agents, Journal of Fluorine Chemistry, Aug. 2006, pp. 1058-1065, vol. 127.
Sakai et al., Chapter 2: Development of Coating Agent for Achieving Water Repellency or Hydrophilicity, Section 3: Development, and Improvement of Performance of Fluorine-derived Coating Agent, Development of Water-repellent Agent, Hydrophilizing Agent and Antifouling Agent, and Control of Coating and Wettability published by Johokiko Co., Ltd., Dec. 22, 2006, pp. 108-121, Japan.

*Primary Examiner* — D. S. Nakarani
(74) *Attorney, Agent, or Firm* — Day Pitney LLP

(57) ABSTRACT

Silane coupling agents which are high in heat resistance, and which are high in durability, releasability, and antifouling properties. The silane coupling agents have a biphenylalkyl group and are represented by the following general formula (1).

(1)

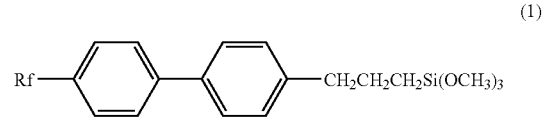

7 Claims, 23 Drawing Sheets

HEAT RESISTANCE OF GLASS SURFACE MODIFIED BY 8F2P3S3M AT 2 HOURS

CHANGE OF CONTACT ANGLE AT 350°C WITH TIME OF GLASS SURFACE MODIFIED BY 8F2P3S3M

SILANE COUPLING AGENTS WITH HEAT RESISTANCE, DURABILITY, RELEASABILITY AND ANTIFOULING PROPERTY, AND PROCESS FOR PRODUCING THESE COMPOUNDS

TECHNICAL FIELD

The present invention relates to heat resistant, durable, releasable and antifouling silane coupling agents having a perfluoroalkyl chain and a biphenylalkyl chain, and a process for producing the silane coupling agents.

BACKGROUND ART

Heretofore, various silane coupling agents have been publicly known. For example, there exists a fluoroalkyl group-containing silane coupling agent having an NCO group that is reactive with a tooth surface. Those expressed by the general formula (9) shown below are publicly known as the specific examples (see Patent Document 1).

$$C_nF_{2n+1}-(X)-SiR_{3-m}(NCO)_m \quad (9)$$

[In the formula (9), X represents $(CH_2)_w$ or $C_6H_4(CH_2)_w$; w represents an integer of 1-4; R represents an alkyl group; n represents an integer of 1-20; and m represents an integer of 1-3.]

A technology is also publicly known in which a sol based on a silane coupling agent having a fluoroalkyl group is coated on an oxide film based on $SiO_2$ formed by a sol-gel process (see Patent Document 2). The silane coupling agent is a fluoroalkyl silane.

Furthermore, an agent to suppress adhesion of polluting substances has been proposed in which a silane coupling agent having fluoroalkyl groups, long chain alkyl groups, and the like is fixed to a base material on which surface concavity and convexity have been formed (see Patent Document 3).

However, conventional silane coupling agents lack heat resistance, and thus heat resistant silane coupling agents usable at high temperatures have been required.

Accordingly, the present inventor has invented a silane coupling agent having a biphenylalkyl group expressed by the general formula (10) shown below (nF2P2S3M) and filed a patent application (see Patent Document 4). The silane coupling agent has high heat resistance so that its contact angle does not decrease even after exposure to an atmosphere of 300° C. for 2 hours or longer.

(10)

[In the formula (10), Rf represents a perfluoroalkyl group of $F(CF_2)_n$; and n represents an integer of 1-12.]

It has been found from subsequent research that the silane coupling agent expressed by the general formula (10) is a mixture of an α-adduct and a β-adduct.

The structural formulas of the α-adduct and β-adduct of nF2P2S3M are shown in FIG. 1.

The ratio between the α-adduct and β-adduct changes depending on carbon number of perfluoroalkyl groups and reaction temperature.

It was also difficult to separate the α-adduct and β-adduct since their boiling points are close.

When the mixture is directly used for surface modification of glass, high heat resistance, durability, releasability, and antifouling property are derived due to π-π interaction (π-π stacking) between benzene rings at the modified surface; however, it has been found that the structure of the modified surface is disordered by the α-adduct and the interaction between benzene rings is considerably weakened.

FIG. 2 shows a schematic view representing the surface modified by 8F2P2S3M in which n=8 in the general formula (10) described above.

It has also been found that only the α-adduct is formed when the reaction temperature during synthesis is of no lower than 100° C.

Patent Document 1: Japanese Unexamined Patent Application No. H09-315923
Patent Document 2: Japanese Unexamined Patent Application No. H10-265242
Patent Document 3: Japanese Unexamined Patent Application No. 2000-342602
Patent Document 4: Japanese Unexamined Patent Application No. 2004-107274
Non-Patent Document 1: Journal of Fluorine Chemistry 127, (2006) 1058-1065
Non-Patent Document 2: Dec. 22, 2006, published by Johokiko Co., 1st edit., "Development of Water-Repellent, Hydrophilic, Antifouling Agent and Control of Coating and Wettability", "3rd section, Development and Performance Advances of Fluorine-Containing Coating Agent", pages 108-121

DISCLOSURE OF THE INVENTION

Problems to be Solved by the Invention

The present invention has been made in view of the problems described above; it is an object of the present invention to provide a heat resistant silane coupling agent having excellent physical properties so that heat resistance, durability, releasability, and antifouling property are further improved, in particular the contact angle of surfaces modified by these compounds does not decrease even at a temperature of at least 350° C.

Means for Solving the Problems

It has been found in accordance with the present invention that the silane coupling agent having a biphenylalkyl group expressed by the general formula (1) shown below has excellent heat resistance, durability, releasability, and antifouling property.

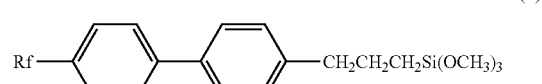
(1)

[In the formula (1), Rf represents a perfluoroalkyl group of $F(CF_2)_n$; wherein n is an integer of 1-14, preferably 1-12, more preferably 4-12, and still more preferably 4-10.]

Effects of the Invention

The silane coupling agent having a biphenylalkyl chain, produced by the production process of the present invention, are high in heat resistance, such that surfaces modified with these compounds show no decrease in contact angle when exposed to an atmosphere having a temperature of 350° C. or higher for 4 hours or longer, and are high in durability, releasability, and antifouling properties, thus significant effects and availability are derived.

PREFERRED MODE FOR CARRYING OUT THE INVENTION

Figure 1:
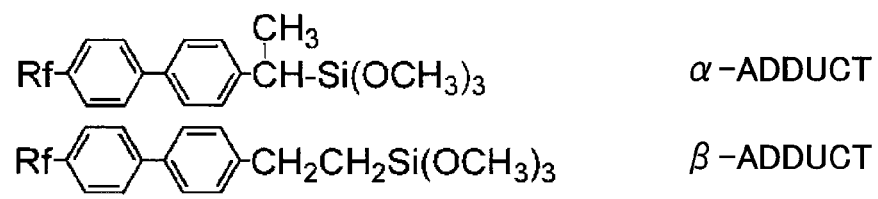
FIG. 1 is a view showing the structural formulas of the α-adduct and β-adduct of nF2P2S3M.
Figure 2:
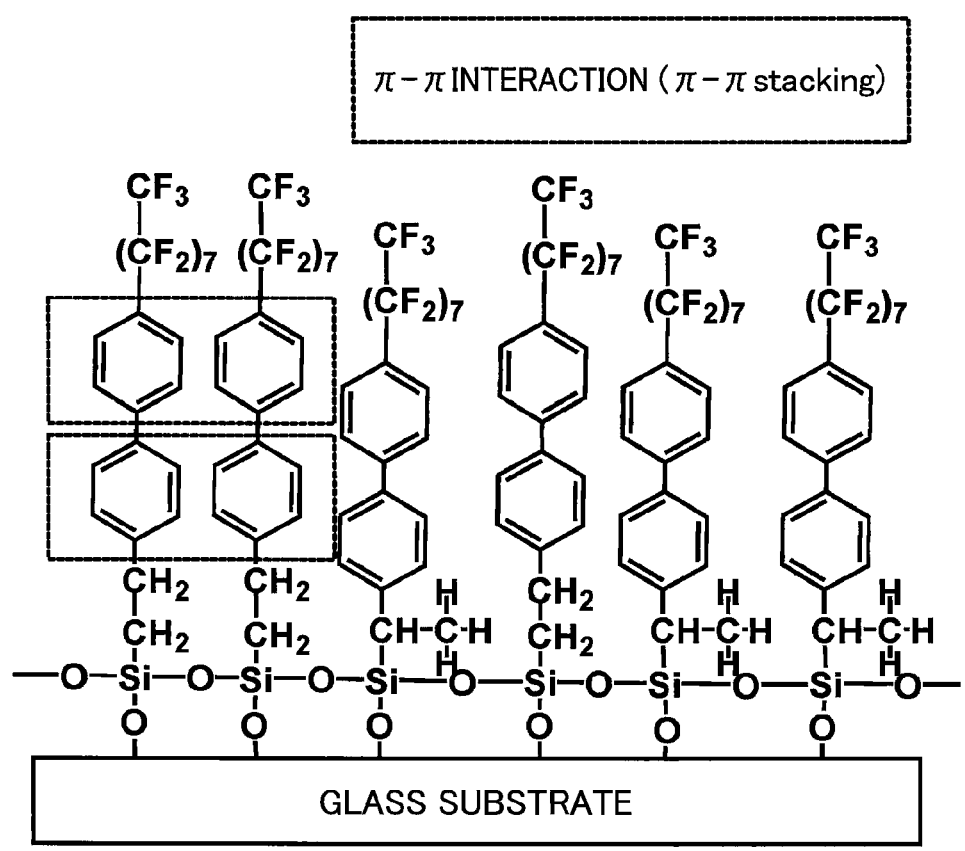
FIG. 2 is a schematic view showing a surface modified by 8F2P2S3M.

There is provided a process for producing a heat resistant, durable, releasable and antifouling silane coupling agent having a perfluoroalkyl group and a biphenylalkyl group, the process including:
a first synthesis step of reacting 4,4'-dibromobiphenyl expressed by general formula (2):

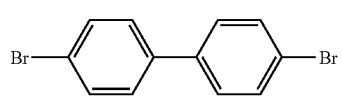
(2)

with a perfluoroalkyl iodide expressed by formula (3):

$F(CF_2)_nI$ (3)

[In the formula (3), n is an integer of 1-14, preferably 1-12, more preferably 4-12, and still more preferably 4-10.]

in a polar solvent using a catalyst of copper bronze powder to obtain 4-perfluoroalkyl-4'-bromobiphenyl expressed by general formula (4):

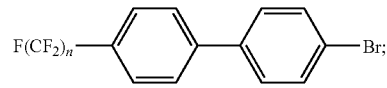
(4)

a second synthesis step of reacting the 4-perfluoroalkyl-4'-bromobiphenyl with an allyl bromide expressed by formula (5)

$CH_2=CHCH_2—Br$ (5)

in a polar solvent using a catalyst of CuI to obtain 4-perfluoroalkyl-4'-allylbiphenyl expressed by general formula (6):

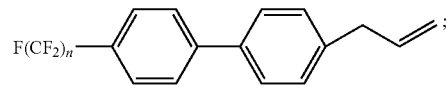
(6)

and, a third synthesis step of reacting the 4-perfluoroalkyl-4'-allylbiphenyl with trimethoxysilane expressed by formula (7):

$HSi(OCH_3)_3$ (7)

in an organic solvent using a catalyst of chloroplatinic acid to obtain (4-perfluoroalkylbiphenyl)propyltrimethoxysilane expressed by general formula (8):

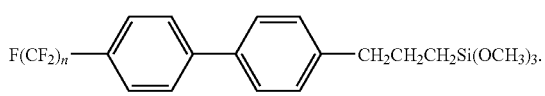
(8)

EXAMPLE 1

The present invention is explained more specifically with reference to examples hereinafter; however, the present invention is not limited to the examples.
Synthesis of 4F2PB of Formula: $F(CF_2)_4(C_6H_4)_2Br$

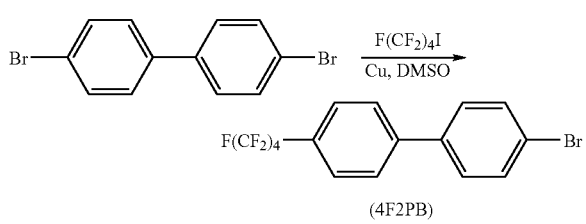
(4F2PB)

A 500 mL round bottom flask, fitted with a reflux condenser and a dripping funnel, was flushed with nitrogen gas to give a nitrogen atmosphere, to which 20.2 g (318 mmol) of copper bronze powder, 24.5 g (74.5 mmol) of 4,4'-dibromobiphenyl, and 120 mL of DMSO as a solvent were added, followed by heating and stirring at 120° C. Two hours later, 26.3 g (76.0 mmol) of perfluorobutyl iodide was slowly added dropwise, followed by heating and stirring at 120° C. for 24 hours. After heating, the solution was cooled to room temperature, and the excess copper bronze powder was removed by filtration using a Kiriyama funnel. CuBr$_2$ and CuI were removed by separation from the filtrate using a saturated NaCl solution, and a distillate was obtained through reduced-pressure distillation after dehydration by magnesium sulfate.

The resulting distillate was analyzed by mass spectroscopy and consequently was identified to be 4F2PB from the peak corresponding to 451 of m/z (molecular weight).

Yield amount: 15.9 g (35 mmol)
Yield rate: 47%
Boiling point: 125° C. to 128° C./31 Pa
Aspect: colorless liquid Synthesis of 4F2PA of Formula: F(CF$_2$)$_4$(C$_6$H$_4$)$_2$CH$_2$CH=CH$_2$

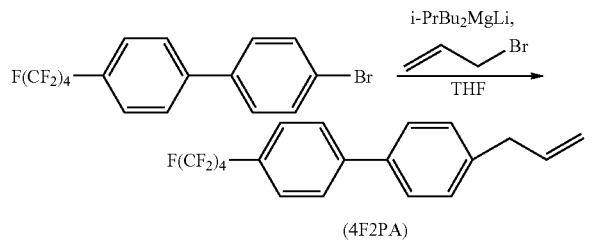

(4F2PA)

A 200 mL round bottom flask, fitted with a dripping funnel, was flushed with nitrogen gas to give a nitrogen atmosphere and cooled by a cooling medium of dry ice/methanol (−78° C.), then 8.0 mL (21.3 mmol) of 2.66 M n-butyllithium/hexane solution was added and subsequently 9.3 mL (12.2 mmol) of 0.76 M isopropylmagnesium bromide/THF solution was added, followed by stirring for 1 hour. Then 4.6 g (10.2 mmol) of 4F2PB dissolved in 50 mL of diethyl ether was slowly added dropwise, followed by stirring at −78° C. for 1 hour, resulting in a brownish yellow solution. After 0.48 g (1.5 mmol) of CuI as a catalyst was added to the brownish yellow solution, 5.5 g (45 mmol) of allyl bromide was added dropwise, followed by stirring for 2 hours. The reaction was stopped by adding a saturated NH$_4$Cl aqueous solution until precipitation ceased. A distillate was obtained through reduced-pressure distillation after dehydration by magnesium sulfate.

The resulting distillate was analyzed by mass spectroscopy and consequently was identified to be 4F2PA from the peak corresponding to 412 of m/z (molecular weight).

Yield amount: 1.86 g (4.5 mmol)
Yield rate: 44%
Boiling point: 155° C. to 158° C./80 Pa
Aspect: colorless liquid Synthesis of 4F2P3S3M of Formula: F(CF$_2$)$_4$(C$_6$H$_4$)$_2$CH$_2$CH$_2$CH$_2$Si(OCH$_3$)$_3$

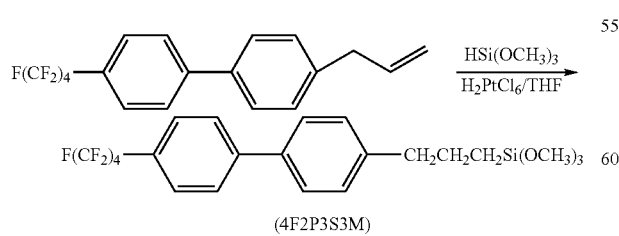

(4F2P3S3M)

A 200 mL round bottom flask, fitted with a reflux condenser, was flushed with nitrogen gas to give a nitrogen atmosphere, to which 10 mL of THF, 1.86 g (4.5 mmol) of 4F2PA, 0.8 g (6.6 mmol) of trimethoxysilane, and 0.1 mL (0.01 mmol) of 0.1 M H$_2$PtCl$_6$/THF solution as a catalyst were added, followed by stirring at 50° C. for 48 hours. After allowing to cool, THF and trimethoxysilane were removed by distillation under reduced pressure. A distillate was obtained through reduced-pressure distillation of the residual material.

The resulting distillate was analyzed by mass spectroscopy and consequently was identified to be 4F2P3S3M from the peak corresponding to 534 of m/z (molecular weight).

Yield amount: 1.60 g (3.0 mmol)
Yield rate: 67%
Boiling point: 151° C. to 153° C./30 Pa
Aspect: colorless liquid

EXAMPLE 2

Synthesis of 6F2PB of Formula: F(cF$_2$)$_6$(C$_6$H$_4$)$_2$Br

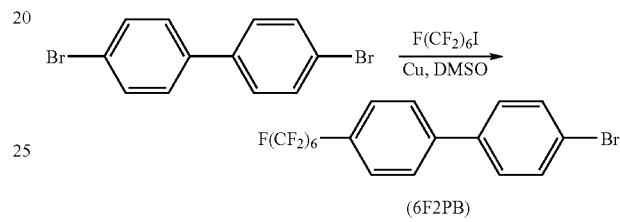

(6F2PB)

A 500 mL round bottom flask, fitted with a reflux condenser and a dripping funnel, was flushed with nitrogen gas to give a nitrogen atmosphere, to which 18.5 g (291 mmol) of copper bronze powder, 23.0 g (73.7 mmol) of 4,4'-dibromobiphenyl, and 120 mL of DMSO as a solvent were added, followed by heating and stirring at 120° C. Two hours later, 33.5 g (75 mmol) of perfluorohexyl iodide was slowly added dropwise, followed by heating and stirring at 120° C. for 24 hours. After heating, the solution was cooled to room temperature, and the excess copper powder was removed by filtration using a Kiriyama funnel. CuBr$_2$ and CuI were removed by separation from the filtrate using a saturated NaCl solution, and a distillate was obtained through reduced-pressure distillation after dehydration by magnesium sulfate.

The resulting distillate was analyzed by mass spectroscopy and consequently was identified to be 6F2PB from the peak corresponding to 551 of m/z (molecular weight).

Yield amount: 19.8 g (36 mmol)
Yield rate: 48%
Boiling point: 130° C. to 132° C./29 Pa
Aspect: colorless liquid Synthesis of 6F2PA of Formula: F(CF$_2$)$_6$(C$_6$H$_4$)$_2$CH$_2$CH=CH$_2$

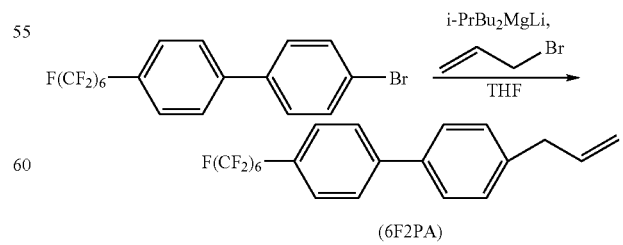

(6F2PA)

A 200 mL round bottom flask, fitted with a dripping funnel, was flushed with nitrogen gas to give a nitrogen atmosphere and cooled by a cooling medium of dry ice/methanol (−78°

C.), then 7.4 mL (19.7 mmol) of 2.66 M n-butyllithium/hexane solution was added and subsequently 11.8 mL (9.0 mmol) of 0.76 M isopropylmagnesium bromide/THF solution was added, followed by stirring for 1 hour. Then 5.20 g (9.4 mmol) of 6F2PB dissolved in 50 mL of diethyl ether was slowly added dropwise, followed by stirring at −78° C. for 1 hour, resulting in a brownish yellow solution. After 0.45 g (1.4 mmol) of CuI as a catalyst was added to the brownish yellow solution, 5.7 g (47 mmol) of allyl bromide was added dropwise, followed by stirring for 2 hours, then the reaction was stopped by adding a saturated NH$_4$Cl aqueous solution until precipitation ceased. A distillate was obtained through reduced-pressure distillation after dehydration by magnesium sulfate.

The resulting distillate was analyzed by mass spectroscopy and consequently was identified to be 6F2PA from the peak corresponding to 512 of m/z (molecular weight).

Yield amount: 2.0 g (4.0 mmol)
Yield rate: 43%
Boiling point: 164° C. to 167° C./80 Pa
Aspect: colorless liquid Synthesis of 6F2P3S3M of Formula: $F(CF_2)_6(C_6H_4)_2CH_2CH_2CH_2Si(OCH_3)_3$

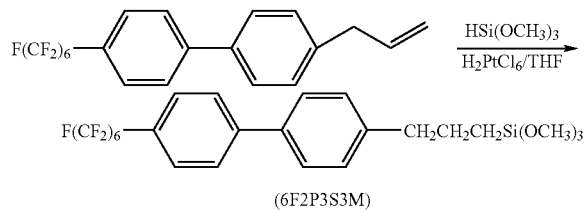

(6F2P3S3M)

A 200 mL round bottom flask, fitted with a reflux condenser, was flushed with nitrogen gas to give a nitrogen atmosphere, to which 10 mL of THF, 2.0 g (4.0 mmol) of 6F2PA, 1.0 g (8.2 mmol) of trimethoxysilane, and 0.1 mL (0.01 mmol) of 0.1 M H$_2$PtCl$_6$/THF solution as a catalyst were added, followed by stirring at 50° C. for 48 hours. After allowing to cool, THF and trimethoxysilane were removed by distillation under reduced pressure. A distillate was obtained through reduced-pressure distillation of the residual material.

The resulting distillate was analyzed by mass spectroscopy and consequently was identified to be 6F2P3S3M from the peak corresponding to 634 of m/z (molecular weight).

Yield amount: 1.40 g (2.73 mmol)
Yield rate: 68%
Boiling point: 155° C. to 161° C./29 Pa
Aspect: colorless liquid

EXAMPLE 3

Synthesis of 8F2PB of Formula: $F(CF_2)_8(C_6H_4)_2Br$

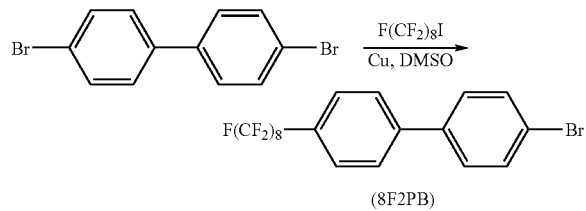

(8F2PB)

A 500 mL round bottom flask, fitted with a reflux condenser and a dripping funnel, was flushed with nitrogen gas to give a nitrogen atmosphere, to which 23.0 g (362 mmol) of copper bronze powder, 25.0 g (80.1 mmol) of 4,4'-dibromobiphenyl, and 120 mL of DMSO as a solvent were added, followed by heating and stirring at 120° C. Two hours later, 23.6 mL (80.5 mmol) of perfluorooctyl iodide was slowly added dropwise, followed by heating and stirring at 120° C. for 24 hours. After heating, the solution was cooled to room temperature, and the excess copper bronze powder and a white solid were removed by filtration using a Kiriyama funnel. The resulting mixture of copper bronze powder and white solid was subjected to soxhlet extraction using ethyl acetate as a solvent. CuBr$_2$ and CuI, existing in the extraction liquid, were removed by separation using a saturated NaCl aqueous solution, and the extraction liquid was subjected to dehydration by magnesium sulfate, and ethyl acetate was removed by distillation under reduced pressure. The residual material was purified through reduced-pressure distillation to obtain a distillate.

Figure 3:
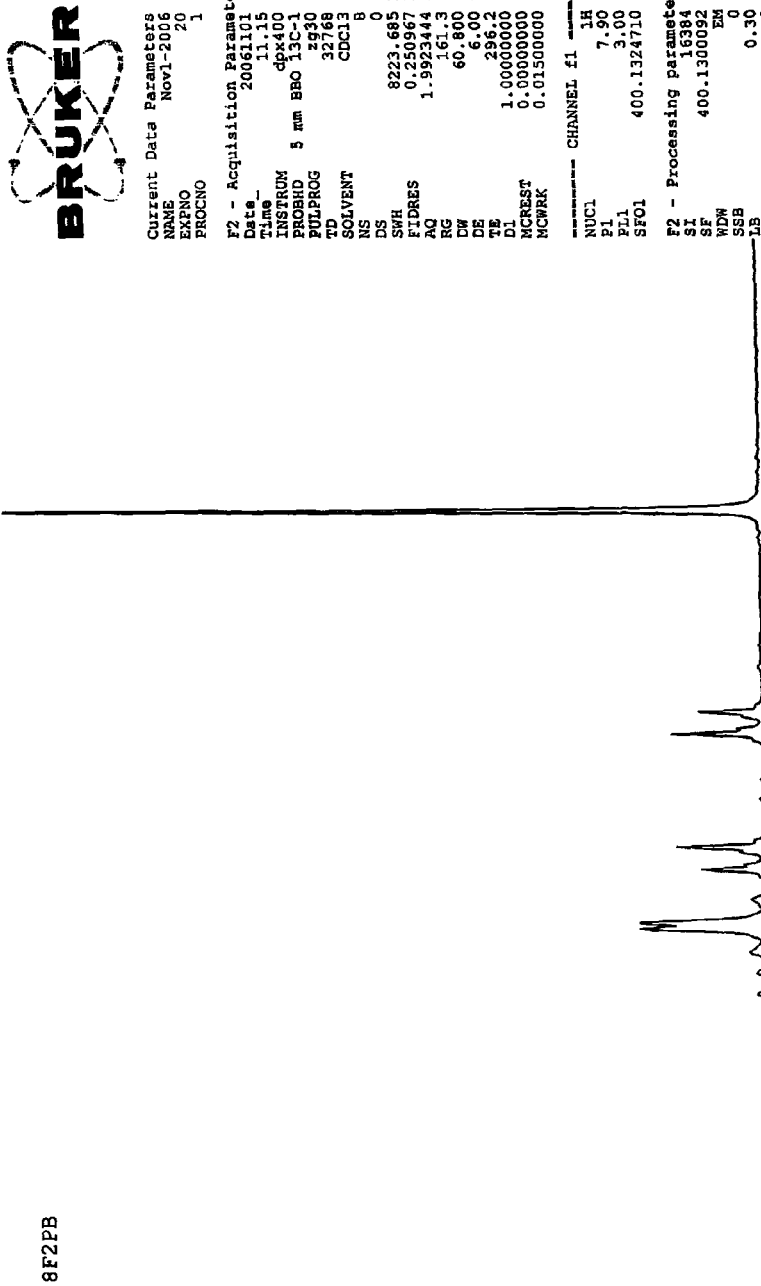
FIG. 3 is a NMR spectrum of 8F2PB (Example 3)
Figure 4:
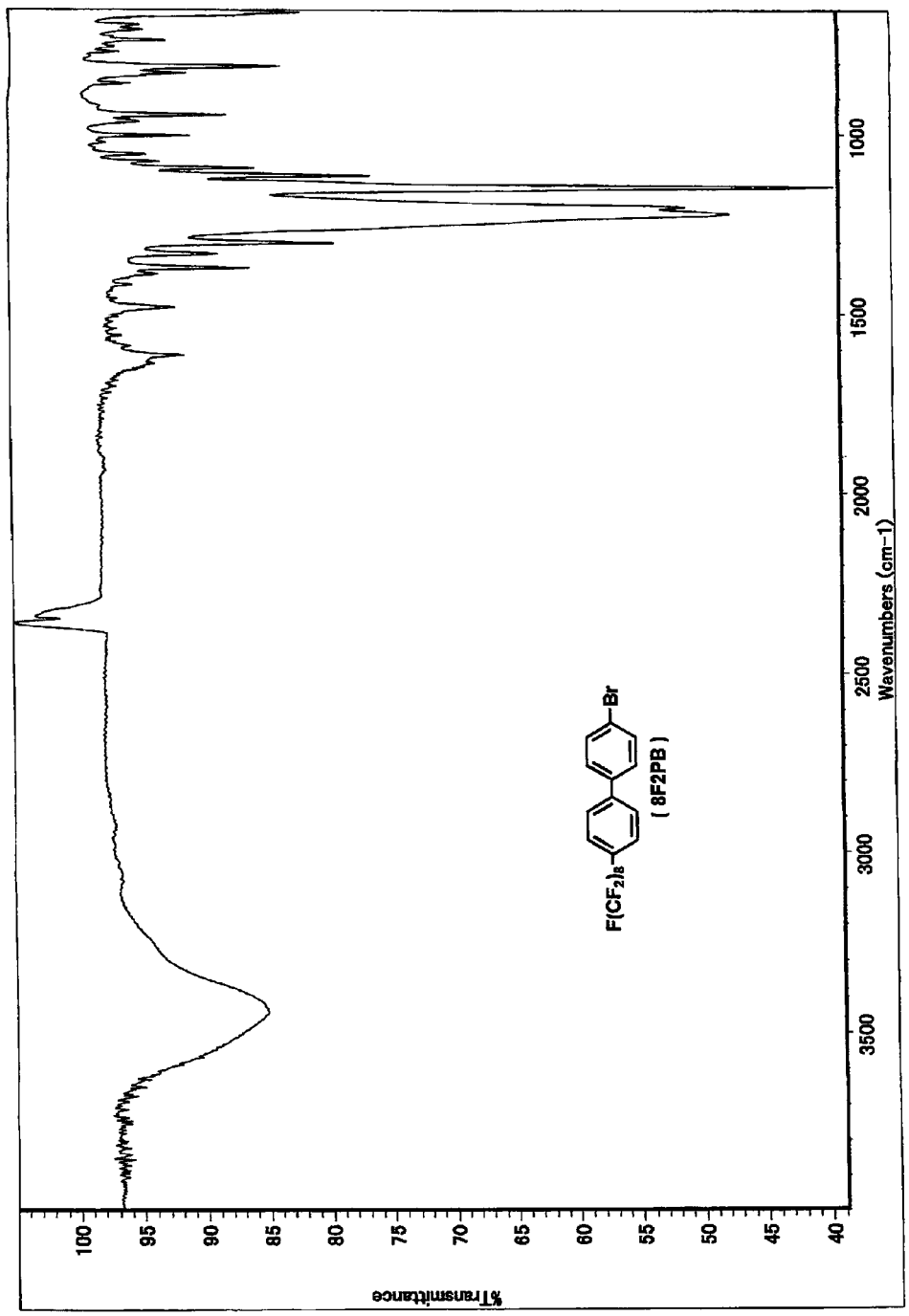
FIG. 4 is an IR spectrum of 8F2PB (Example 3)
Figure 5:
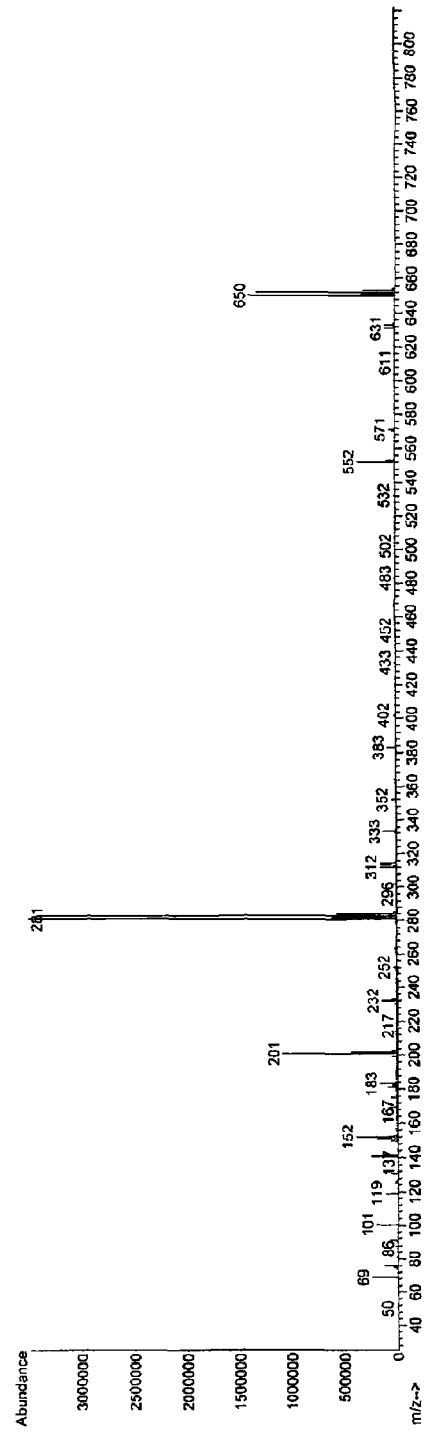
FIG. 5 is a mass spectrum of 8F2PB (Example 3)

The resulting distillate was analyzed by $^1$H-NMR, FT-IR, and mass spectroscopy. The NMR, IR, and mass spectra are respectively shown in FIGS. 3, 4 and 5.

The resulting distillate was identified to be 8F2PB from the $^1$H-NMR, FT-IR, and mass (m/z: 651) spectra.

Yield amount: 22.9 g (35.2 mmol)
Yield rate: 44%
Boiling point: 134° C. to 135° C./30 Pa
Aspect: white solid Synthesis of 8F2PA of Formula: $F(CF_2)_8(C_6H_4)_2CH_2CH=CH_2$

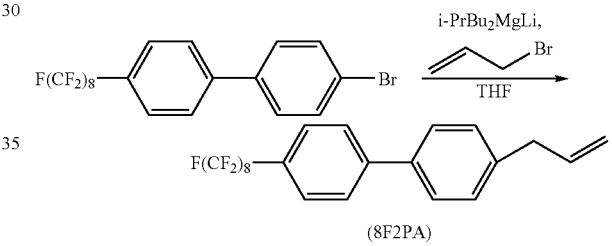

(8F2PA)

A 200 mL round bottom flask, fitted with a dripping funnel, was flushed with nitrogen gas to give a nitrogen atmosphere and cooled by a cooling medium of dry ice/methanol (−78° C.), to which 6.79 mL (18.1 mmol) of 2.66 M n-butyllithium/hexane solution was added and subsequently 11.9 mL (9.04 mmol) of 0.76 M isopropylmagnesium bromide/THF solution was added, followed by stirring for 1 hour. Then 4.80 g (7.40 mmol) of 8F2PB dissolved in 50 mL of diethyl ether was slowly added dropwise, followed by stirring at −78° C. for 1 hour, resulting in a brownish yellow solution. After 0.42 g (22.2 mmol) of CuI as a catalyst was added to the brownish yellow solution, 3.82 mL (45.18 mmol) of allyl bromide was added dropwise, followed by stirring for 2 hours, then the reaction was stopped by adding a saturated NH$_4$Cl aqueous solution until precipitation ceased. After extraction by ethyl acetate, an extraction liquid was subjected to dehydration by magnesium sulfate, and ethyl acetate was removed under reduced pressure. The residual material was purified through reduced-pressure distillation to obtain a distillate.

Figure 6:
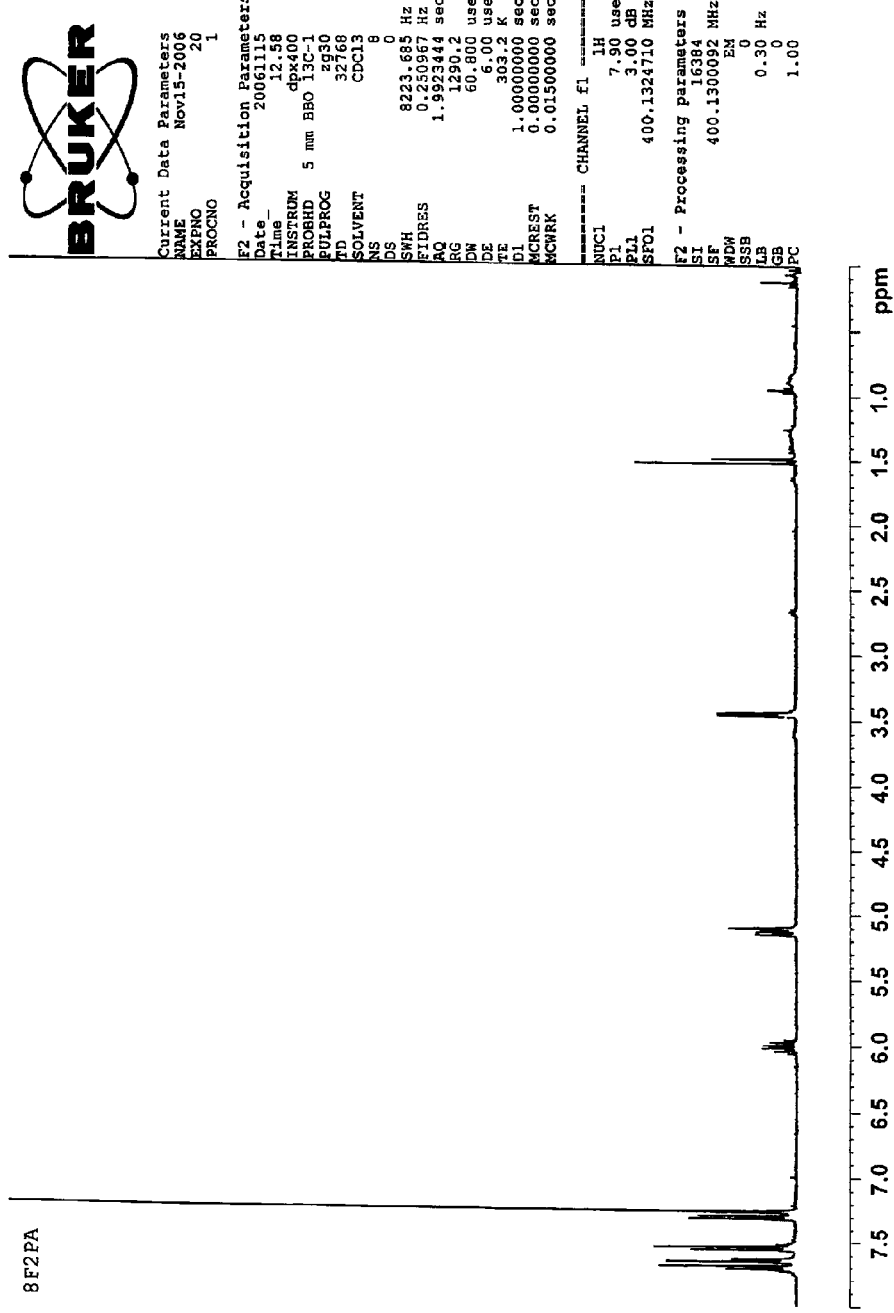
FIG. 6 is a NMR spectrum of 8F2PA (Example 3)
Figure 7:
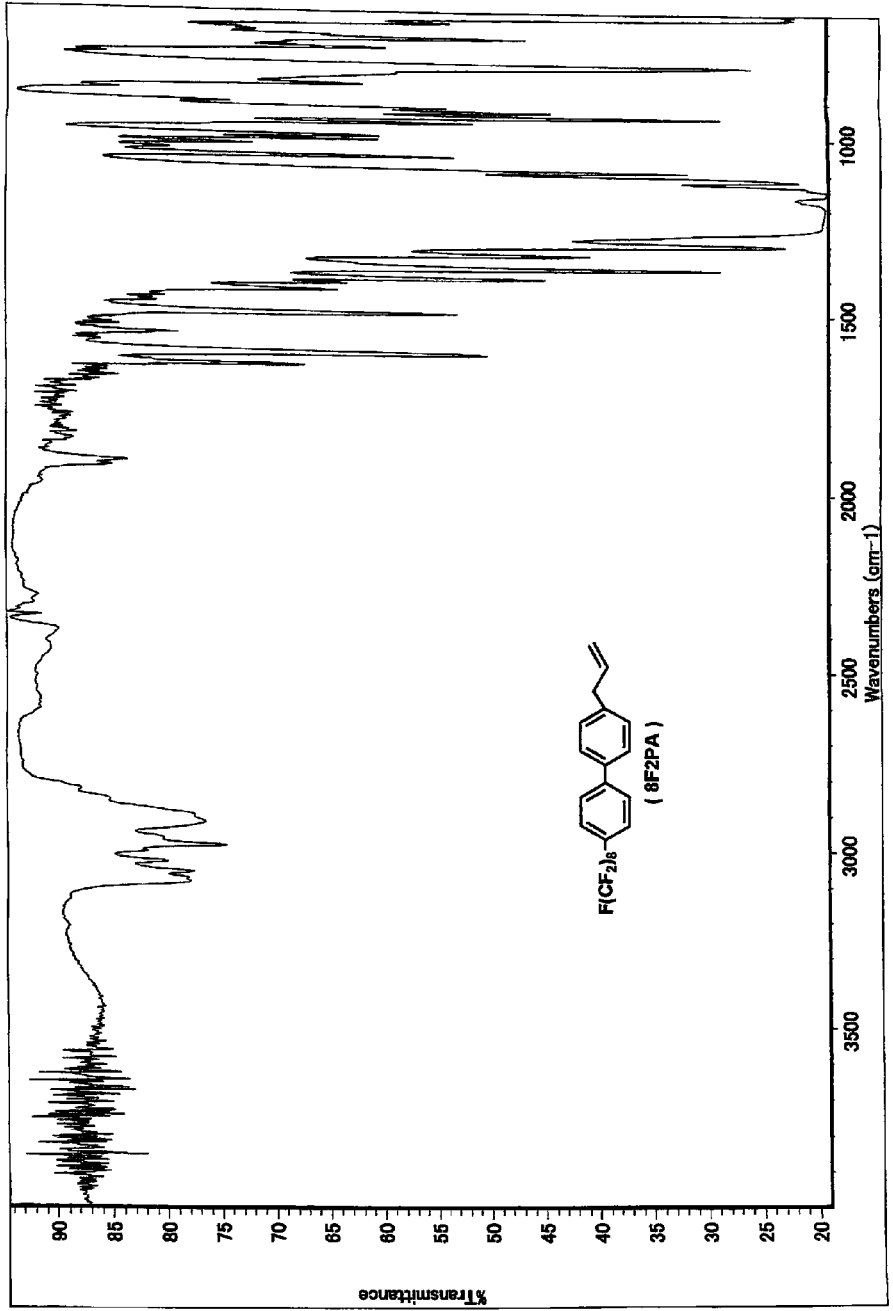
FIG. 7 is an IR spectrum of 8F2PA (Example 3)
Figure 8:
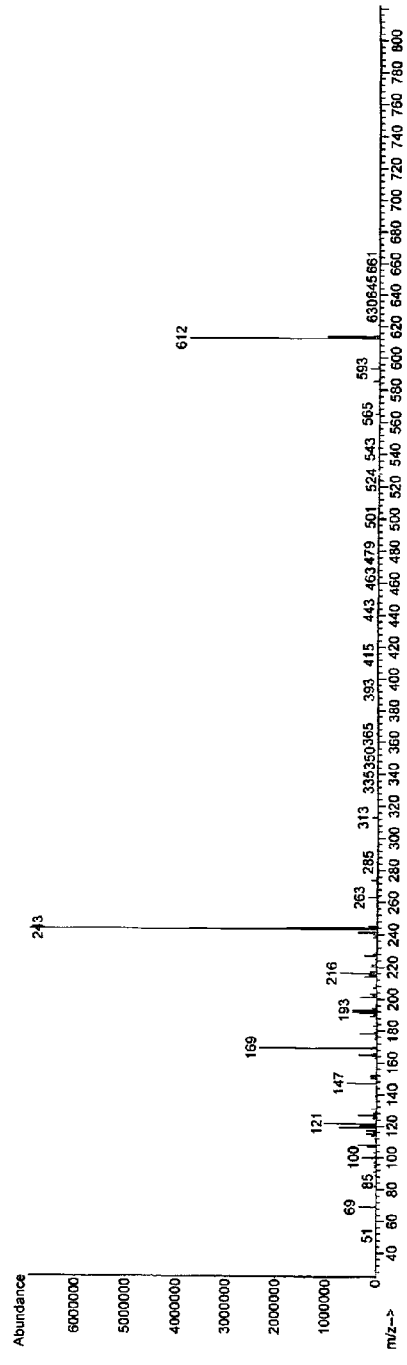
FIG. 8 is a mass spectrum of 8F2PA (Example 3)

The resulting distillate was analyzed by $^1$H-NMR, FT-IR, and mass spectroscopy. The NMR, IR, and mass spectra are respectively shown in FIGS. 6, 7 and 8.

The resulting distillate was identified to be 8F2PA from the $^1$H-NMR, FT-IR, and mass (m/z: 612) spectra.

Yield amount: 1.86 g (3.04 mmol)
Yield rate: 41%
Boiling point: 164° C. to 167° C./80 Pa
Aspect: white solid Synthesis of 8F2P3S3M of Formula: $F(CF_2)_8(C_6H_4)_2CH_2CH_2CH_2Si(OCH_3)_3$

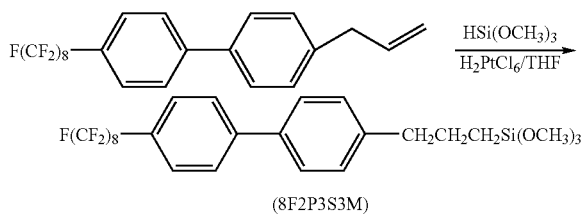

(8F2P3S3M)

A 200 mL round bottom flask, fitted with a reflux condenser, was flushed with nitrogen gas to give a nitrogen atmosphere, to which 10 mL of THF, 1.86 g (3.04 mmol) of 8F2PA, 0.77 g (6.08 mmol) of trimethoxysilane, and 0.1 mL (0.01 mmol) of 0.1 M $H_2PtCl_6$/THF solution as a catalyst were added, followed by stirring at 50° C. for 48 hours. After allowing to cool, THF and trimethoxysilane were removed by distillation under reduced pressure. The residual material was purified through reduced-pressure distillation to obtain a distillate.

Figure 9:
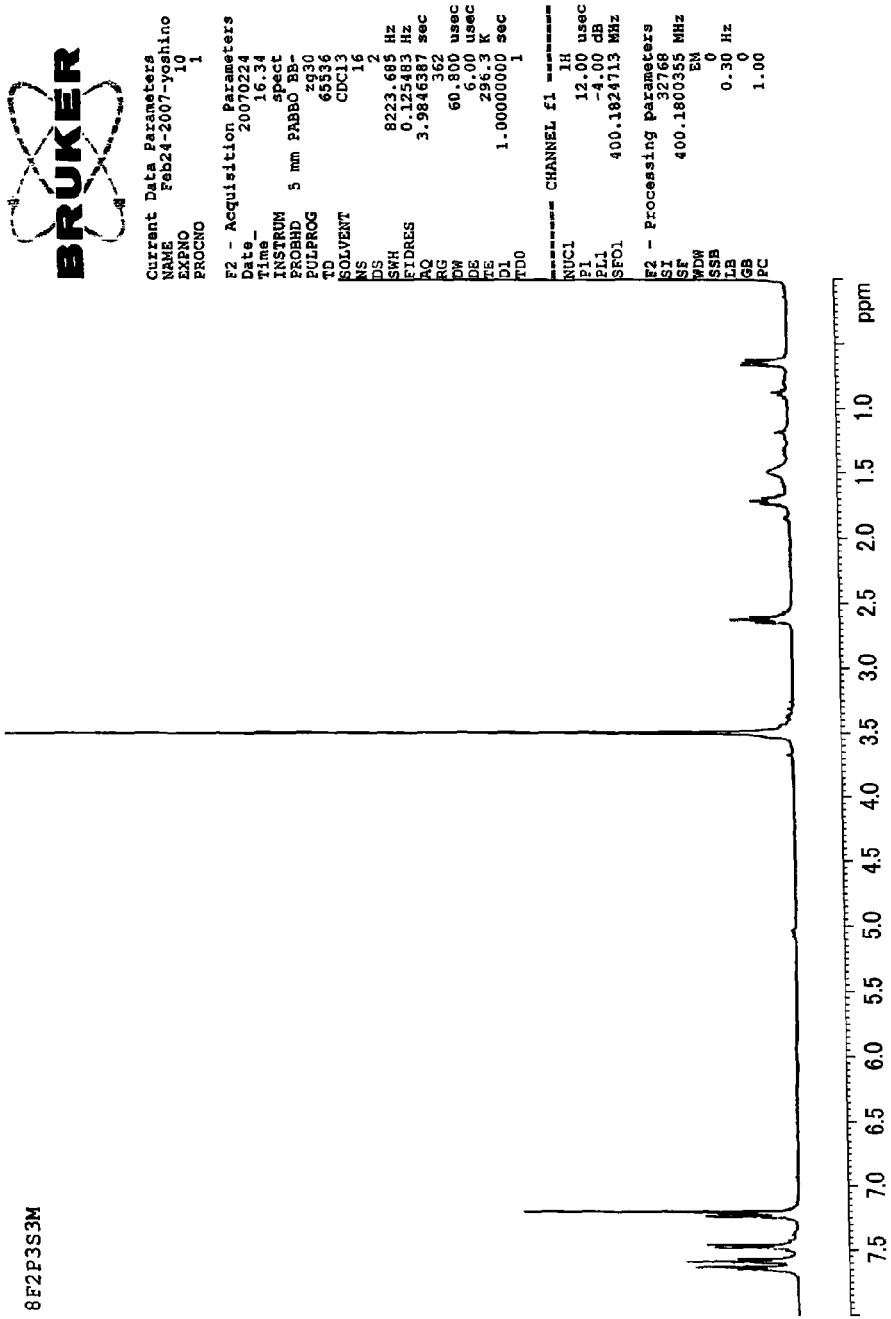
FIG. 9 is a NMR spectrum of 8F2P3S3M (Example 3)
Figure 10:
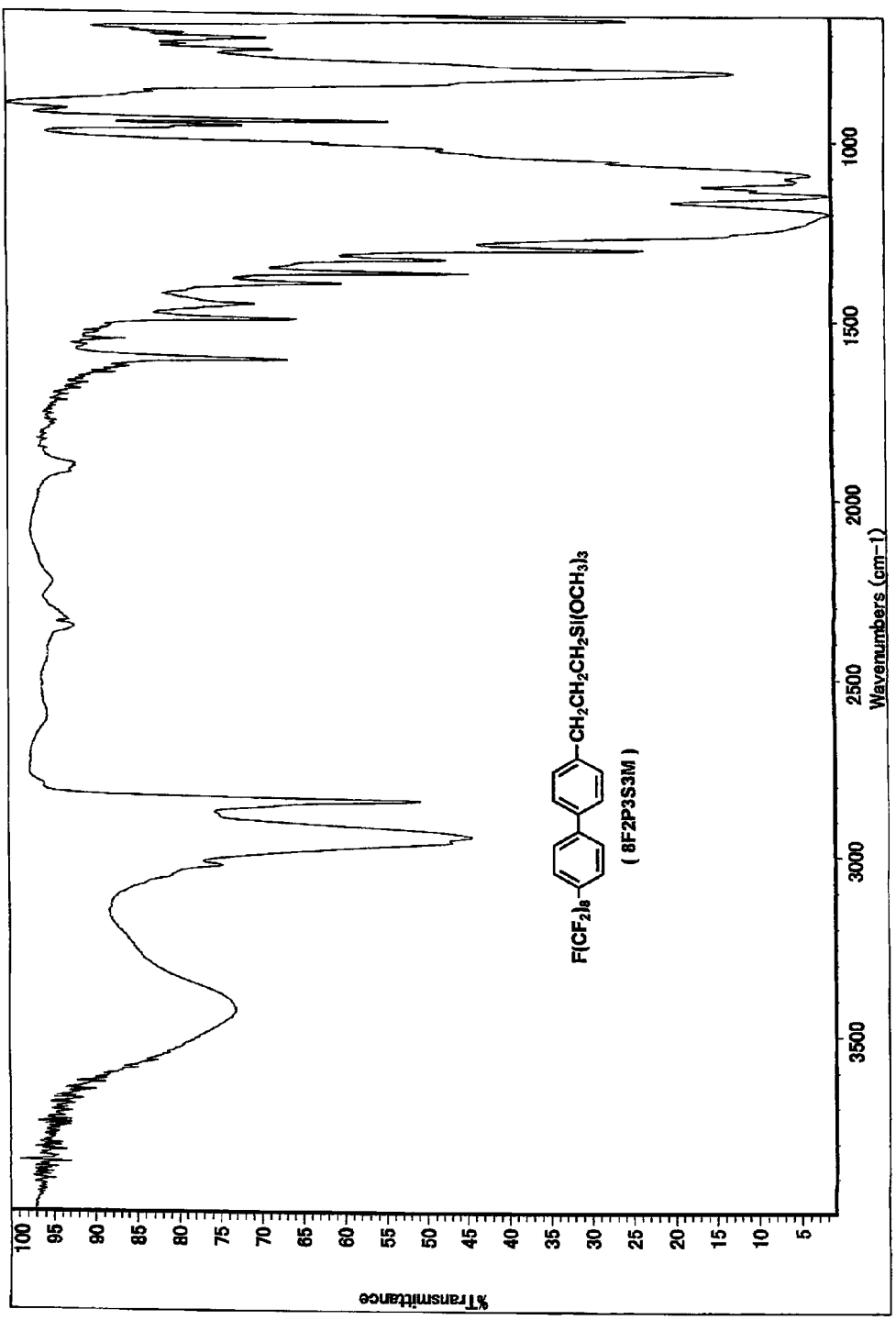
FIG. 10 is an IR spectrum of 8F2P3S3M (Example 3)
Figure 11:
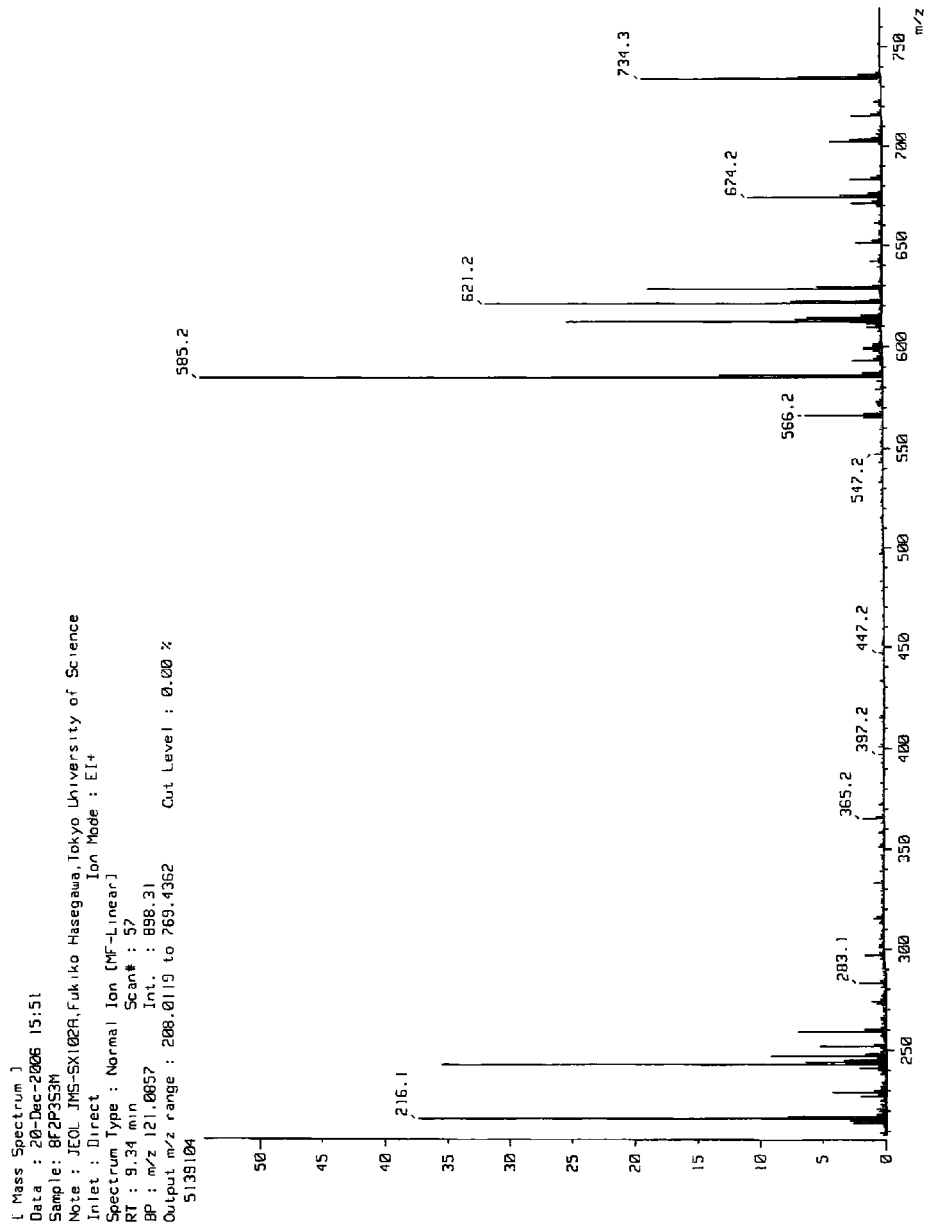
FIG. 11 is a mass spectrum of 8F2P3S3M (Example 3)

The resulting distillate was analyzed by $^1$H-NMR, FT-IR, and mass spectroscopy. The NMR, IR, and mass spectra are respectively shown in FIGS. 9, 10 and 11.

The resulting distillate was identified to be 8F2P3S3M from the $^1$H-NMR, FT-IR, and mass spectra.

Yield amount: 1.50 g (2.04 mmol)
Yield rate: 67%
Boiling point: 160° C. to 165° C./30 Pa
Aspect: white solid

EXAMPLE 4

Synthesis of 10F2PB of Formula: $F(CF_2)_{10}(C_6H_4)_2Br$

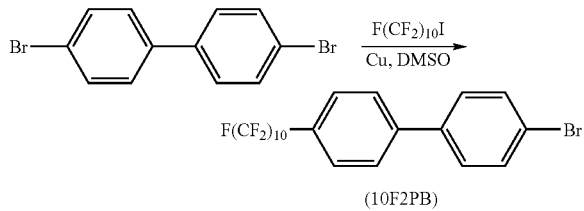

(10F2PB)

A 500 mL round bottom flask, fitted with a reflux condenser and a dripping funnel, was flushed with nitrogen gas to give a nitrogen atmosphere, to which 20.0 g (315 mmol) of copper bronze powder, 20.0 g (64.1 mmol) of 4,4'-dibromobiphenyl, and 120 mL of DMSO as a solvent were added, followed by heating and stirring at 120° C. Two hours later, 42.6 g (66 mmol) of perfluorodecyl iodide was slowly added dropwise, followed by heating and stirring at 120° C. for 24 hours. After heating, the solution was cooled to room temperature, and the excess copper bronze powder and a white solid were removed by filtration using a Kiriyama funnel. The resulting mixture of copper bronze powder and white solid was subjected to soxhlet extraction using ethyl acetate as a solvent. $CuBr_2$ and CuI, existing in the extraction liquid, were removed by separation using a saturated NaCl aqueous solution, and the extraction liquid was subjected to dehydration by magnesium sulfate, and ethyl acetate was removed by distillation under reduced pressure. A distillate was obtained through reduced-pressure distillation of the residual material.

Figure 12:
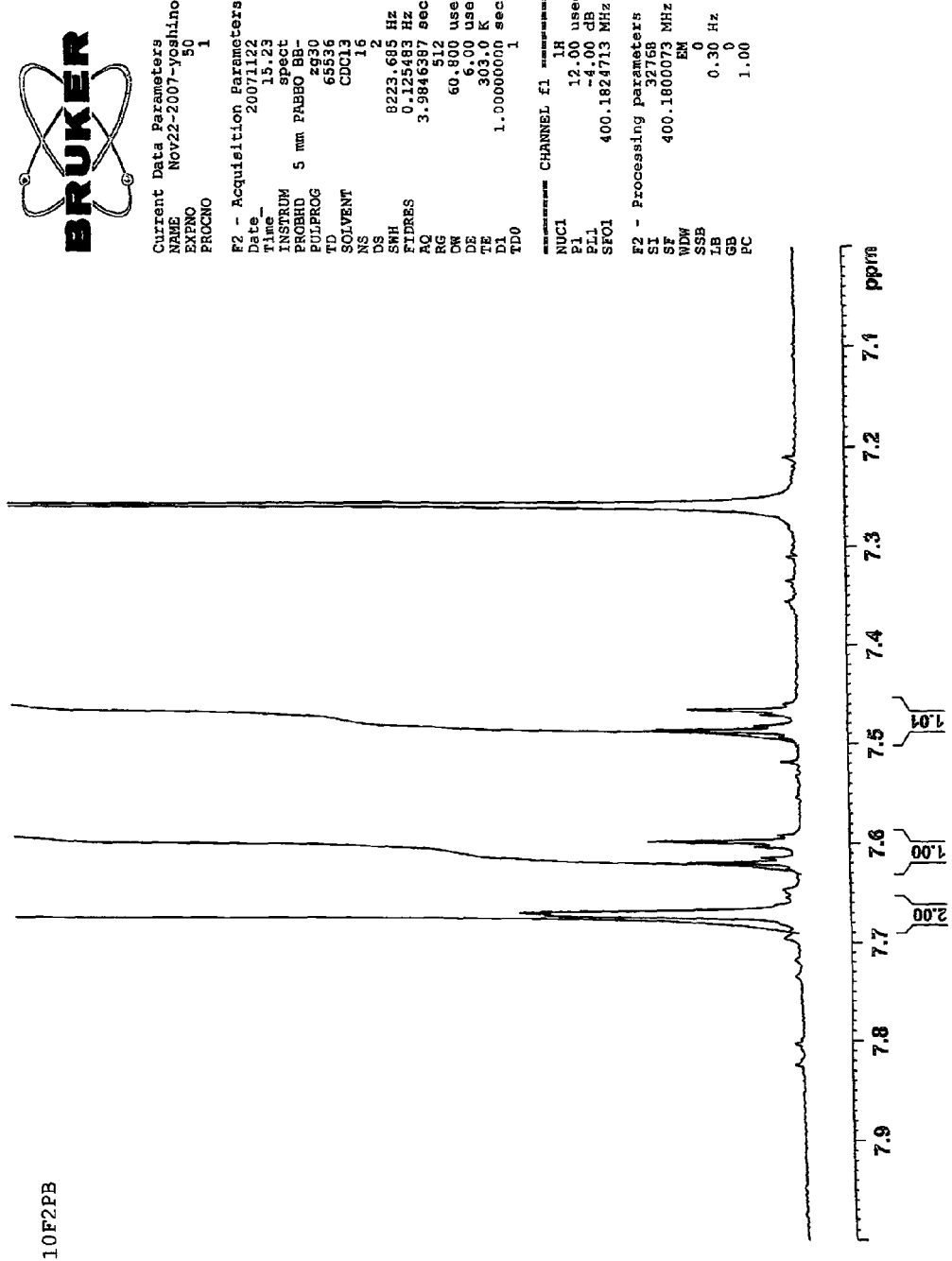
FIG. 12 is a NMR spectrum of 10F2PB (Example 4)
Figure 13:
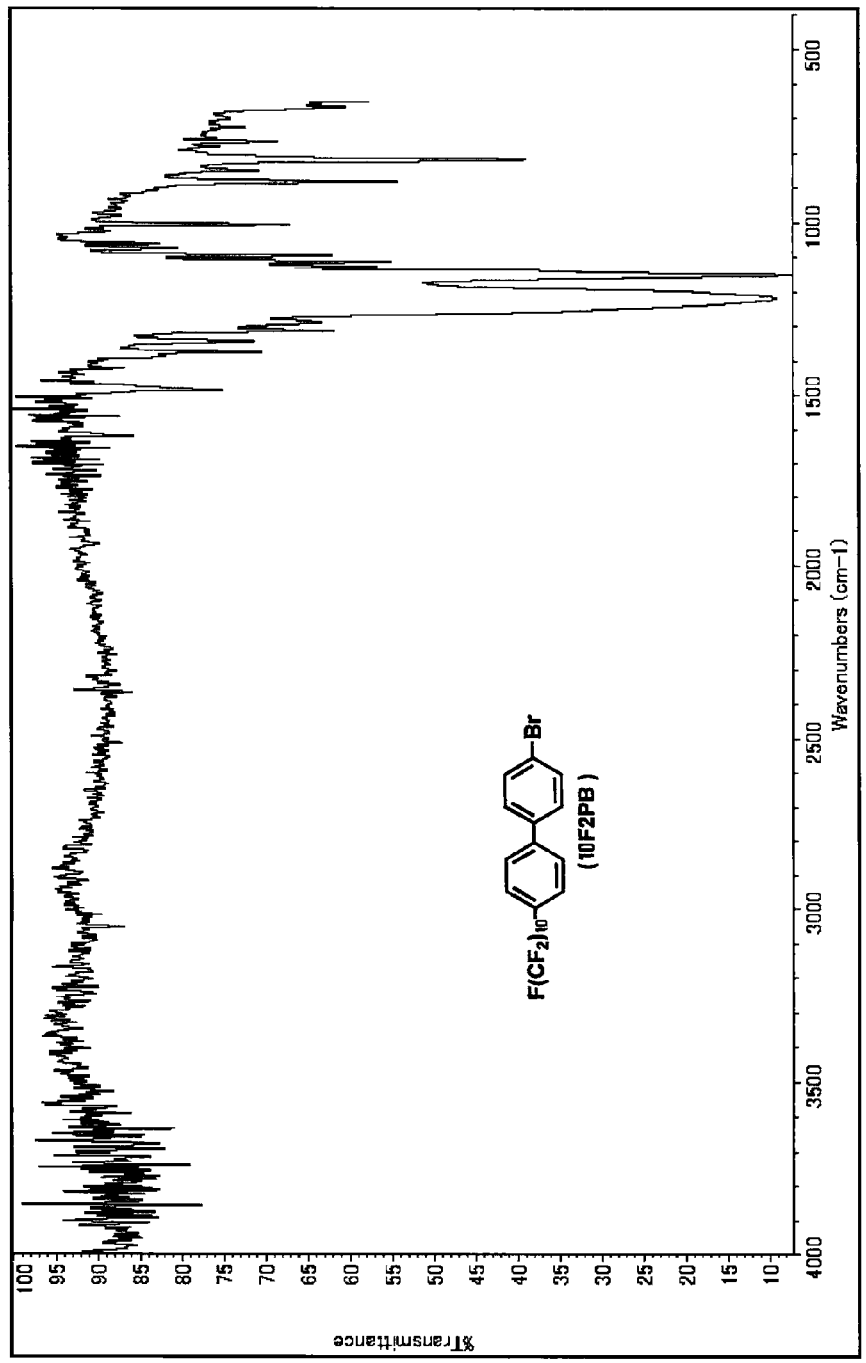
FIG. 13 is an IR spectrum of 10F2PB (Example 4)
Figure 14:
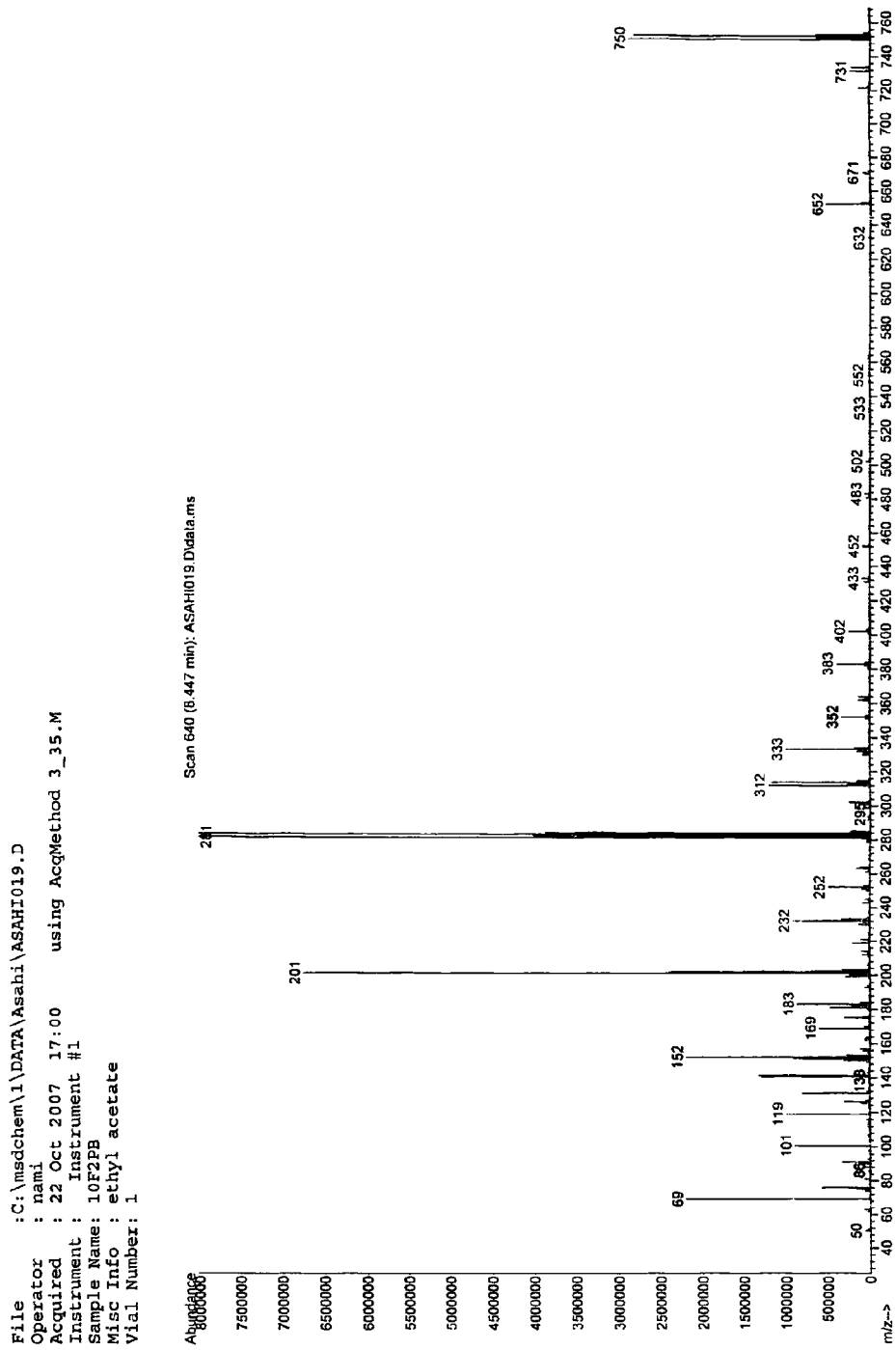
FIG. 14 is a mass spectrum of 10F2PB (Example 4)

The resulting distillate was analyzed by $^1$H-NMR, FT-IR, and mass spectroscopy. The NMR, IR, and mass spectra are respectively shown in FIGS. 12, 13 and 14.

The resulting distillate was identified to be 10F2PB from the $^1$H-NMR, FT-IR, and mass (m/z: 751) spectra.

Yield amount: 28.2 g (37.5 mmol)
Yield rate: 65%
Boiling point: 139° C. to 143° C./32 Pa
Aspect: white solid Synthesis of 10F2PA of Formula: $F(CF_2)_{10}(C_6H_4)_2CH_2CH=CH_2$

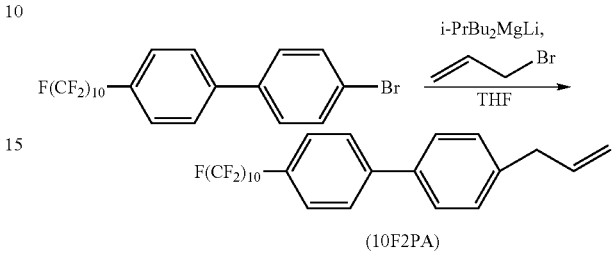

(10F2PA)

A 200 mL round bottom flask, fitted with a dripping funnel, was flushed with nitrogen gas to give a nitrogen atmosphere, to which 7.2 mL (19.2 mmol) of 2.66 M n-butyllithium/hexane solution was added while cooling on ice and subsequently 12.3 mL (9.3 mmol) of 0.76 M isopropylmagnesium bromide/THF solution was added, followed by stirring for 1 hour. Then 5.27 g (7.40 mmol) of 10F2PB dissolved in 50 mL of diethyl ether was slowly added dropwise, followed by stirring for 1 hour while cooling on ice, resulting in a brownish yellow solution. After 0.5 g (1.6 mmol) of CuI as a catalyst was added to the brownish yellow solution, 5.4 g (45 mmol) of allyl bromide was added dropwise, followed by stirring for 2 hours, then the reaction was stopped by adding a saturated $NH_4Cl$ aqueous solution until precipitation ceased. After extraction by ethyl acetate, an extraction liquid was subjected to dehydration by magnesium sulfate, and ethyl acetate was removed under reduced pressure. A distillate was obtained through reduced-pressure distillation of the residual material.

Figure 15:
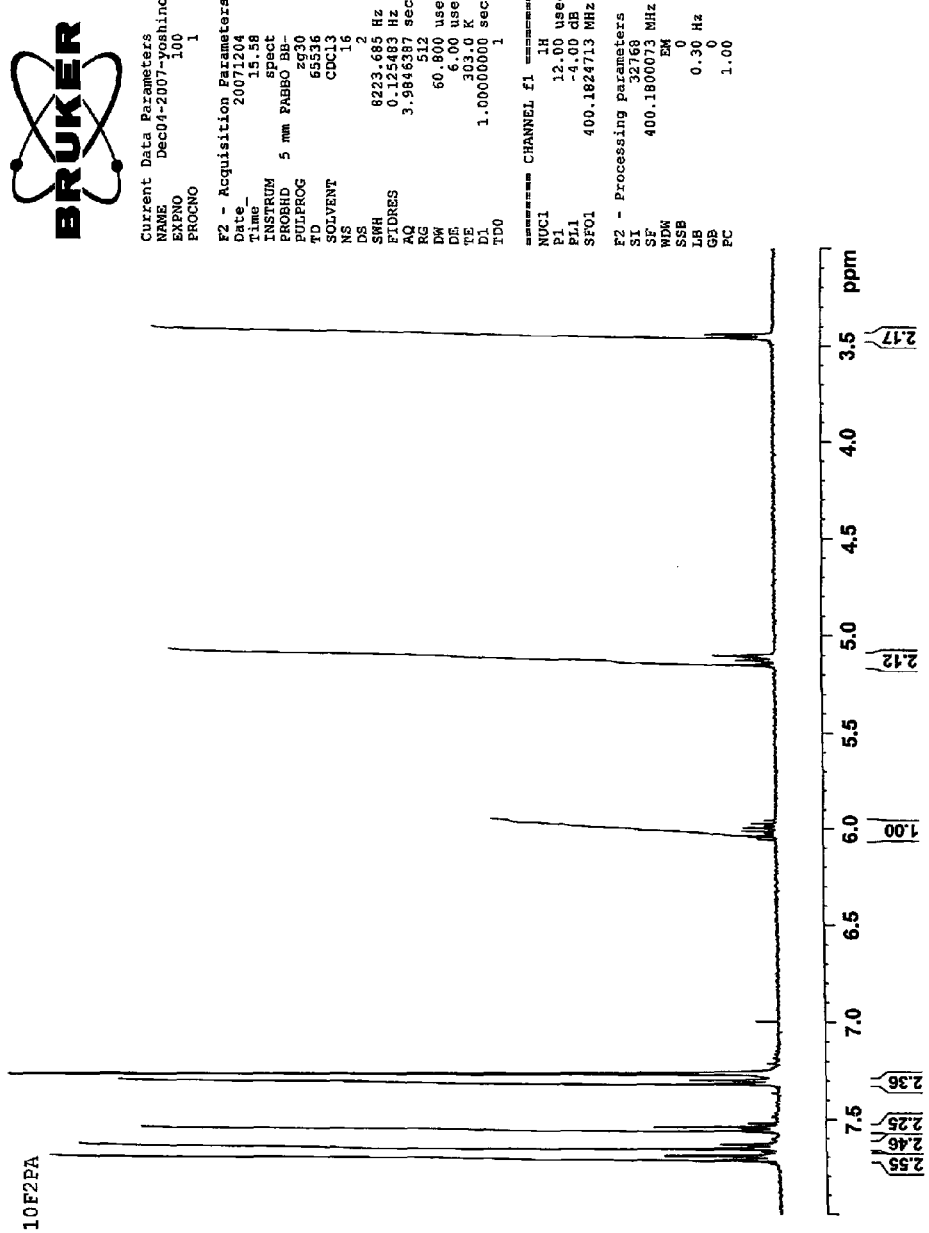
FIG. 15 is a NMR spectrum of 10F2PA (Example 4)
Figure 16:
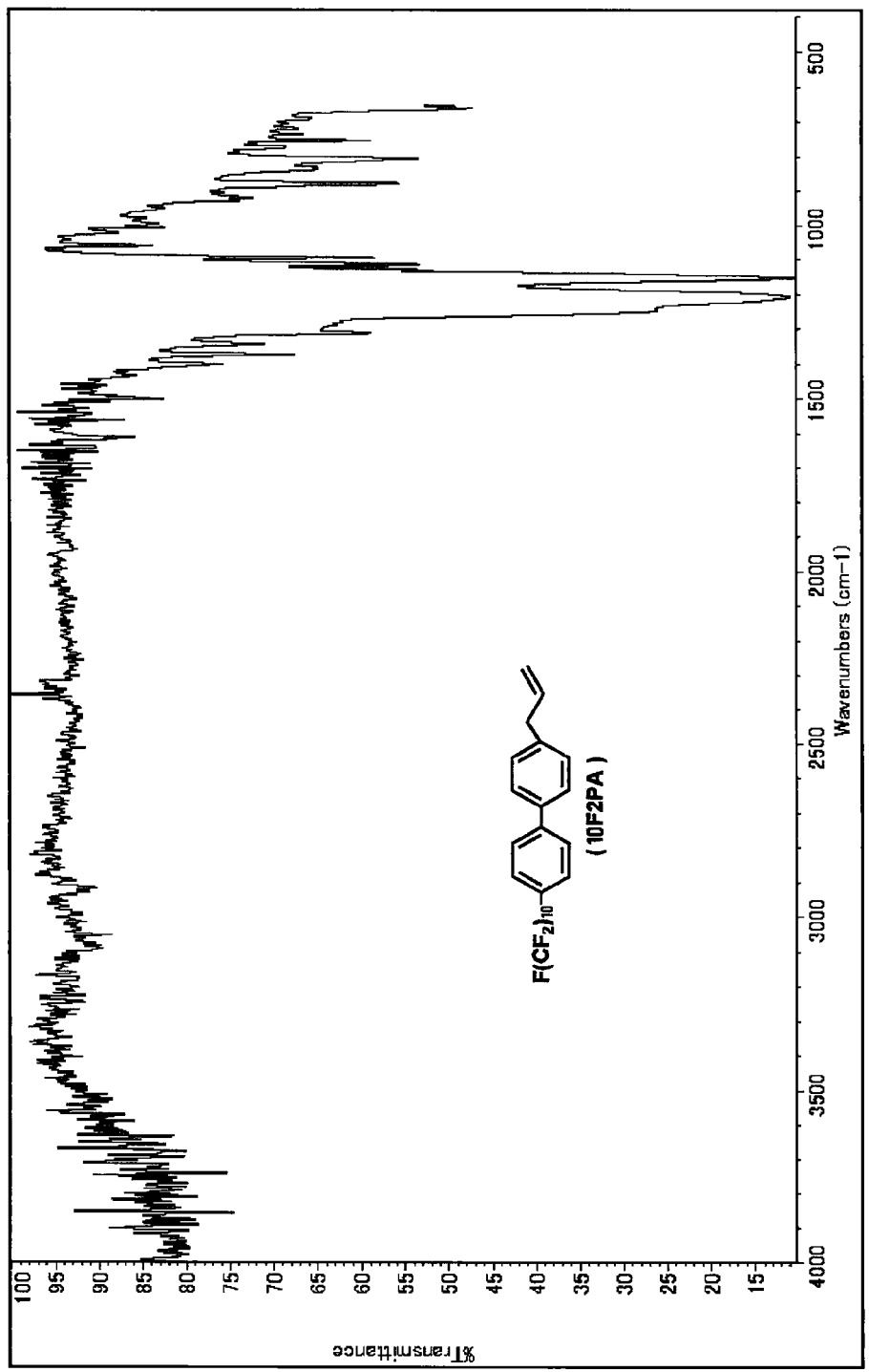
FIG. 16 is an IR spectrum of 10F2PA (Example 4)
Figure 17:
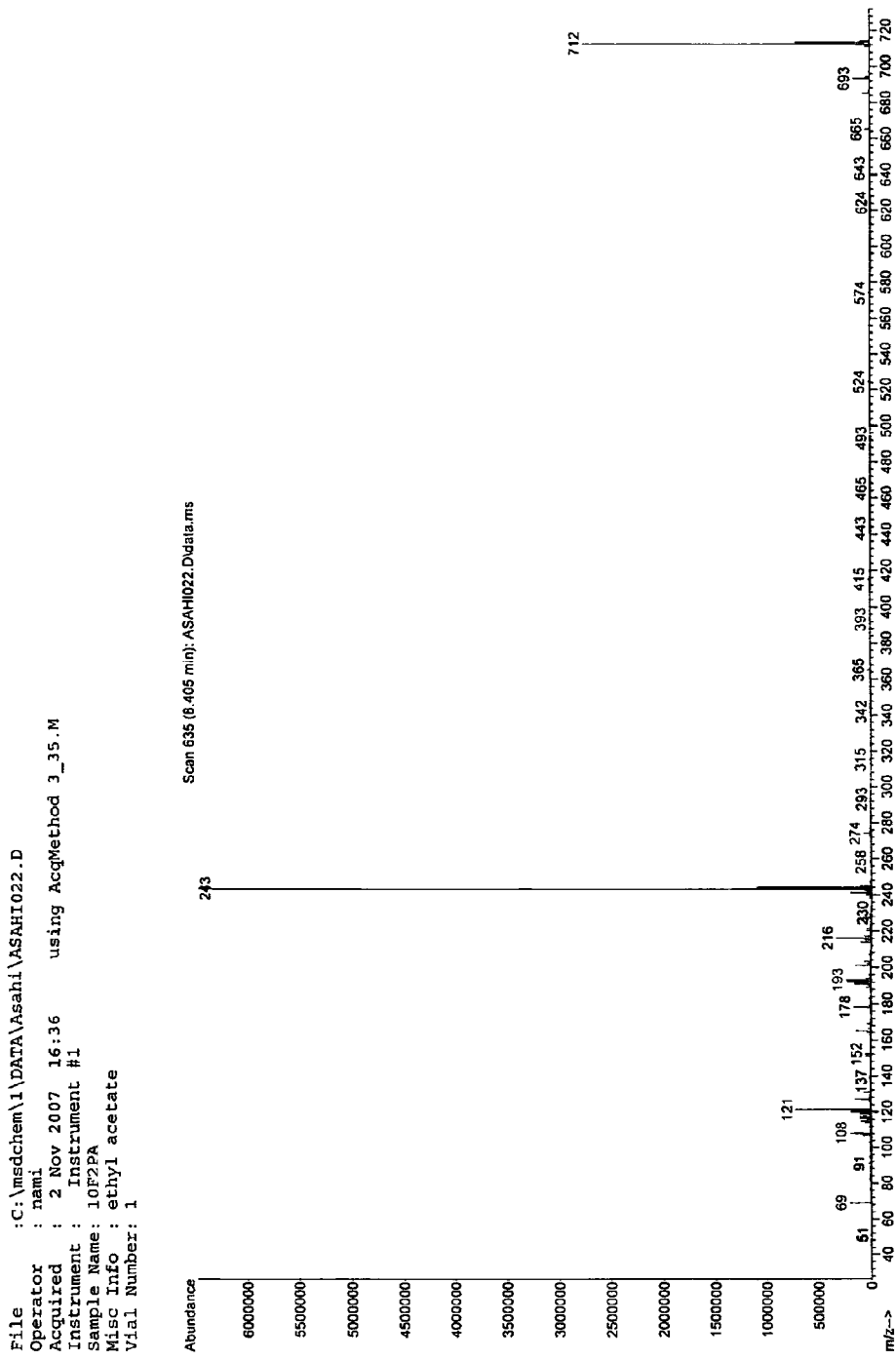
FIG. 17 is a mass spectrum of 10F2PA (Example 4)

The resulting distillate was analyzed by $^1$H-NMR, FT-IR, and mass spectroscopy. The NMR, IR, and mass spectra are respectively shown in FIGS. 15, 16 and 17.

The resulting distillate was identified to be 10F2PA from the $^1$H-NMR, FT-IR, and mass (m/z: 712) spectra.

Yield amount: 2.16 g (3.04 mmol)
Yield rate: 41%
Boiling point: 169° C. to 173° C./77 Pa
Aspect: white solid Synthesis of 10F2P3S3M of Formula:

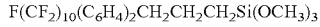

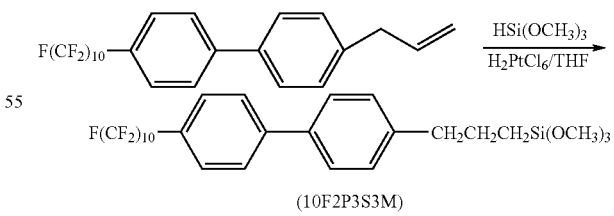

(10F2P3S3M)

A 200 mL round bottom flask, fitted with a reflux condenser, was flushed with nitrogen gas to give a nitrogen atmosphere, to which 10 mL of THF, 2.16 g (3.04 mmol) of 10F2PA, 1.0 g (8.2 mmol) of trimethoxysilane, and 0.1 mL (0.01 mmol) of 0.1 M $H_2PtCl_6$/THF solution as a catalyst were added, followed by stirring at 50° C. for 48 hours. After allowing to cool, THF and trimethoxysilane were removed by distillation under reduced pressure. A distillate was obtained through reduced-pressure distillation of the residual material.

Figure 18:
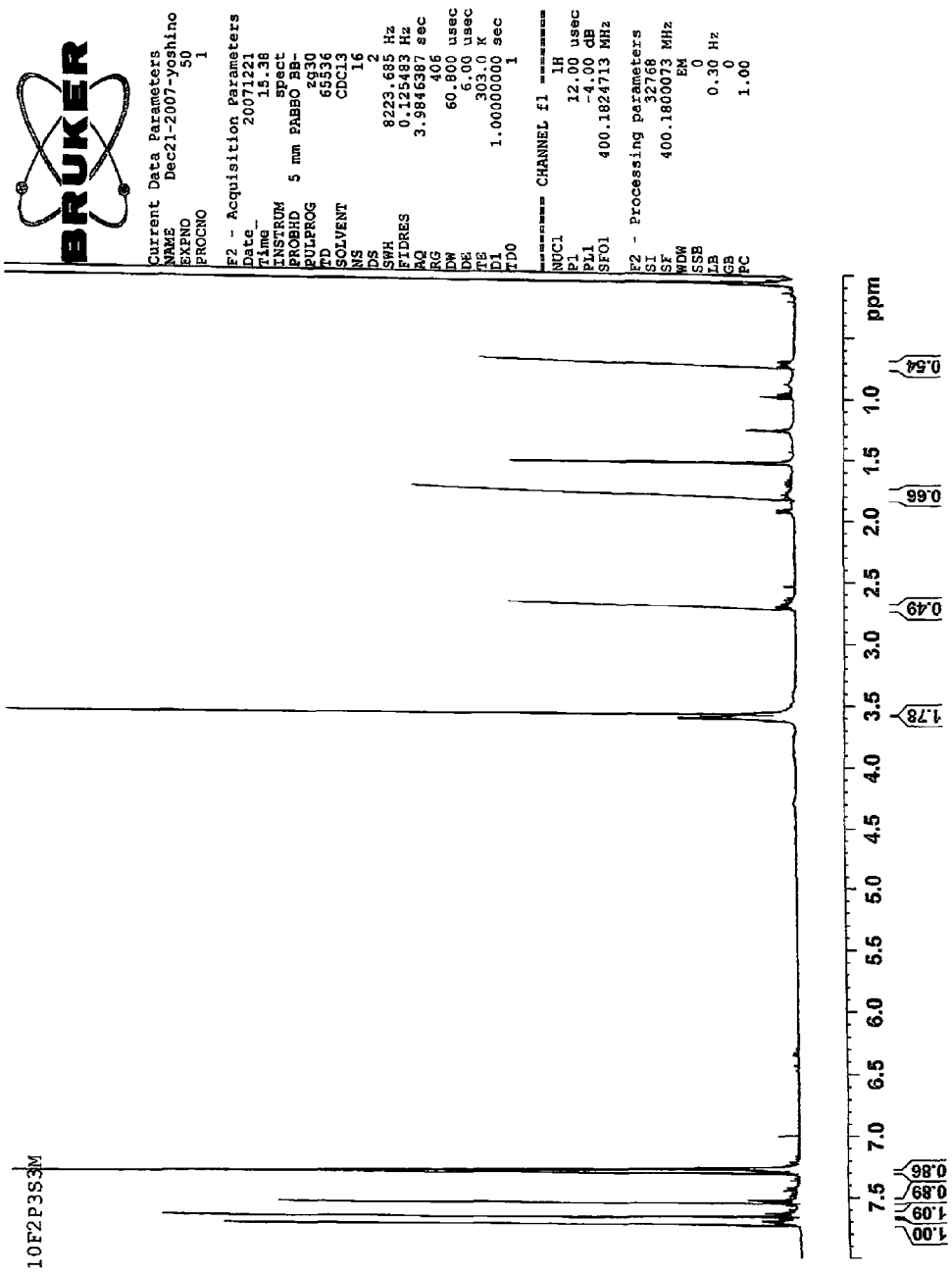
FIG. 18 is a NMR spectrum of 10F2P3S3M (Example 4)
Figure 19:
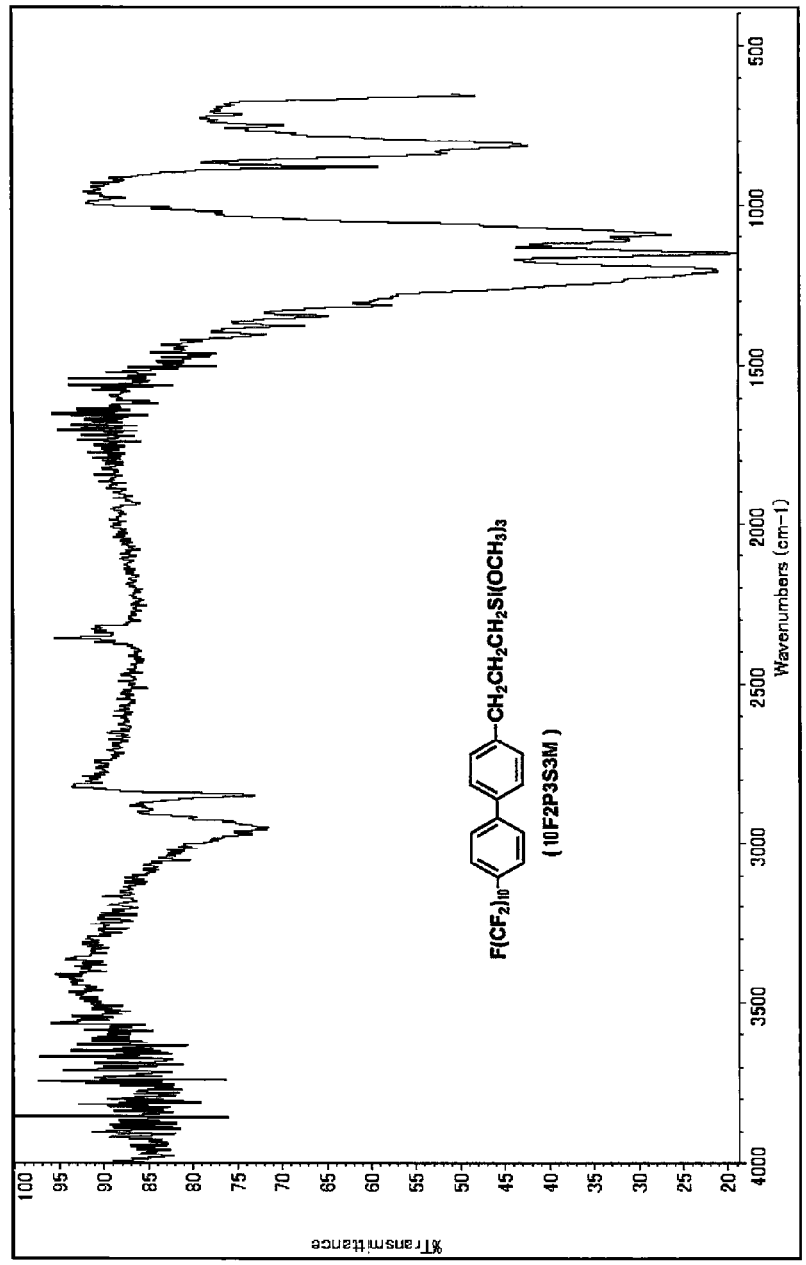
FIG. 19 is an IR spectrum of 10F2P3S3M (Example 4)
Figure 20:
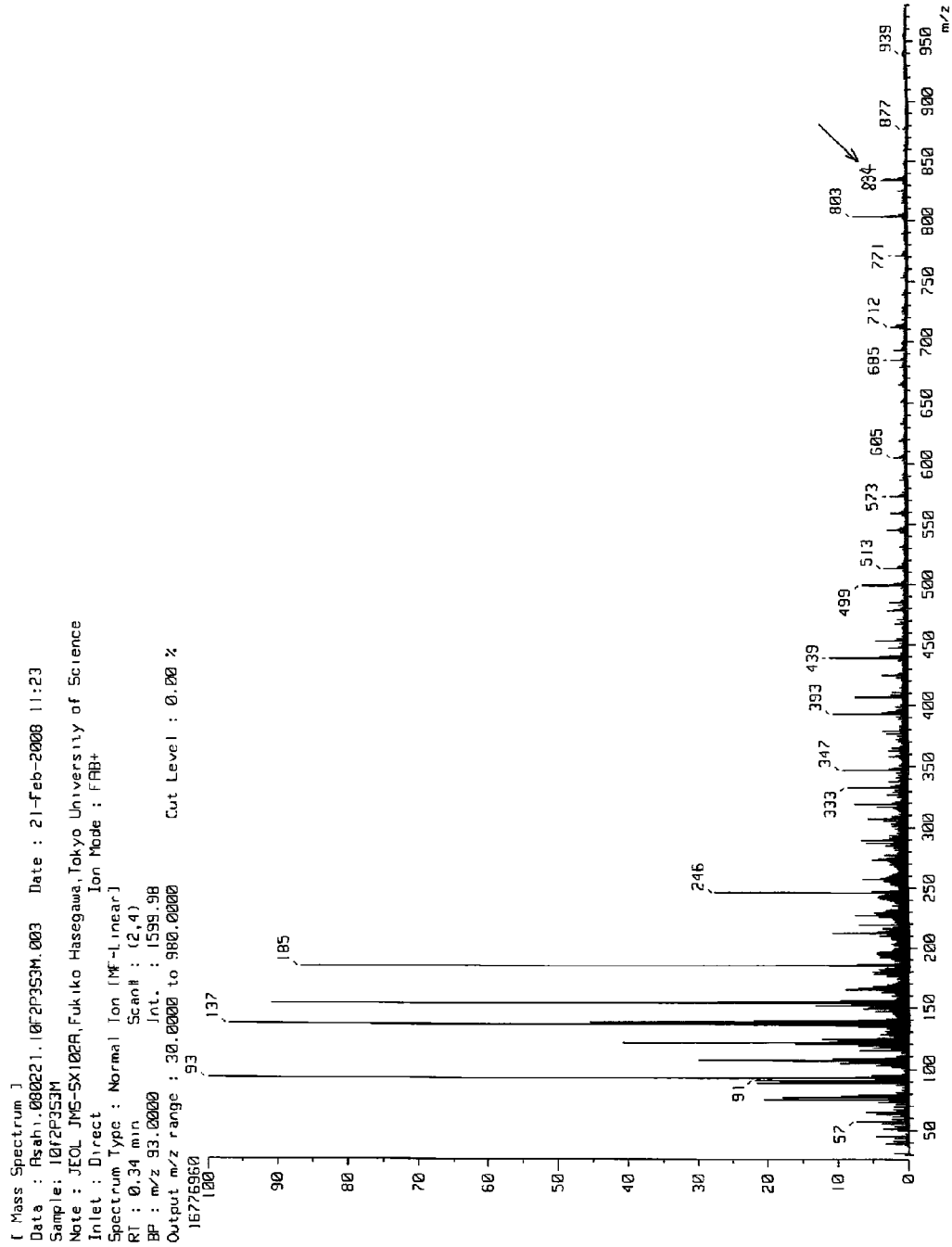
FIG. 20 is a mass spectrum of 10F2P3S3M (Example 4)

The resulting distillate was analyzed by $^1$H-NMR, FT-IR, and mass spectroscopy. The NMR, IR, and mass spectra are respectively shown in FIGS. 18, 19 and 20.

The resulting distillate was identified to be 10F2P3S3M from the $^1$H-NMR, FT-IR, and mass spectra. HRMS=834.1083 (calculated value: 834.5323)

Yield amount: 1.65 g (1.98 mmol)

Yield rate: 65%

Boiling point: 164° C. to 167° C./28 Pa

Aspect: white solid

EXAMPLE 5

Synthesis of 12F2PB of Formula: $F(CF_2)_{12}(C_6H_4)_2Br$

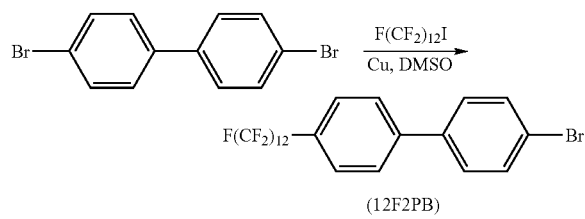

(12F2PB)

A 500 mL round bottom flask, fitted with a reflux condenser and a dripping funnel, was flushed with nitrogen gas to give a nitrogen atmosphere, to which 20.0 g (315 mmol) of copper bronze powder, 20.0 g (64.1 mmol) of 4,4'-dibromobiphenyl, and 120 mL of DMSO as a solvent were added, followed by heating and stirring at 120° C. Two hours later, 49.2 g (66 mmol) of perfluorododecyl iodide was slowly added dropwise, followed by heating and stirring at 120° C. for 24 hours. After heating, the solution was cooled to room temperature, and the excess copper bronze powder and a white solid (10F2PB) were removed by filtration using a Kiriyama funnel. The resulting mixture of copper bronze powder and white solid was subjected to soxhlet extraction using ethyl acetate as a solvent. $CuBr_2$ and CuI, existing in the extraction liquid, were removed by separation using a saturated NaCl aqueous solution, and the extraction liquid was subjected to dehydration by magnesium sulfate, and ethyl acetate was removed by distillation under reduced pressure. A distillate was obtained through reduced-pressure distillation of the residual material.

The resulting distillate was analyzed by mass spectroscopy and consequently was identified to be 12F2PB from the peak corresponding to 851 of m/z (molecular weight).

Yield amount: 35.5 g (41.7 mmol)

Yield rate: 65%

Boiling point: 145° C. to 148° C./30 Pa

Aspect: white solid

Synthesis of 12F2PA of Formula: $F(CF_2)_{12}(C_6H_4)_2CH_2CH=CH_2$

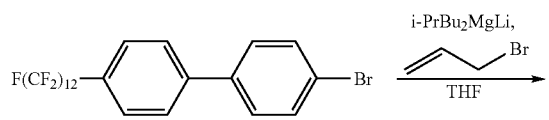

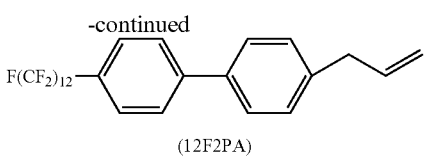

(12F2PA)

A 200 mL round bottom flask, fitted with a dripping funnel, was flushed with nitrogen gas to give a nitrogen atmosphere, to which 7.2 mL (19.2 mmol) of 2.66 M n-butyllithium/hexane solution was added while cooling on ice and subsequently 12.3 mL (9.3 mmol) of 0.76 M isopropylmagnesium bromide/THF solution was added, followed by stirring for 1 hour. Then 6.81 g (8.00 mmol) of 12F2PB dissolved in 50 mL of diethyl ether was slowly added dropwise, followed by stirring for 1 hour while cooling on ice, resulting in a brownish yellow solution. After 0.5 g (1.6 mmol) of CuI as a catalyst was added to the brownish yellow solution, 5.4 g (45 mmol) of allyl bromide was added dropwise, followed by stirring for 2 hours, then the reaction was stopped by adding a saturated $NH_4Cl$ aqueous solution until precipitation ceased. After extraction by ethyl acetate, an extraction liquid was subjected to dehydration by magnesium sulfate, and ethyl acetate was removed under reduced pressure. A distillate was obtained through reduced-pressure distillation of the residual material.

The resulting distillate was analyzed by mass spectroscopy and consequently was identified to be 12F2PA from the peak corresponding to 812 of m/z (molecular weight).

Yield amount: 2.72 g (3.36 mmol)

Yield rate: 42%

Boiling point: 175° C. to 179° C./75 Pa

Aspect: white solid

Synthesis of 12F2P3S3M of Formula:

$F(CF_2)_{12}(C_6H_4)_2CH_2CH_2CH_2Si(OCH_3)_3$

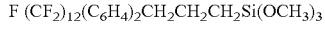
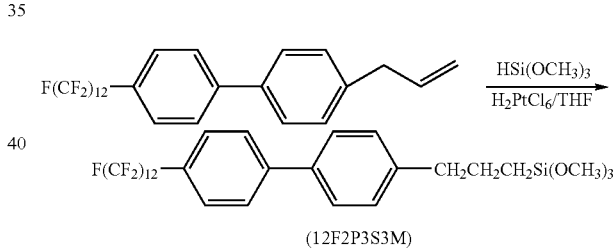

(12F2P3S3M)

A 200 mL round bottom flask, fitted with a reflux condenser, was flushed with nitrogen gas to give a nitrogen atmosphere, to which 10 mL of THF, 2.50 g (3.07 mmol) of 12F2PA, 1.0 g (8.2 mmol) of trimethoxysilane, and 0.1 mL (0.01 mmol) of 0.1 M $H_2PtCl_6$/THF solution as a catalyst were added, followed by stirring at 50° C. for 48 hours. After allowing to cool, THF and trimethoxysilane were removed by distillation under reduced pressure. A distillate was obtained through reduced-pressure distillation of the residual material.

The resulting distillate was analyzed by mass spectroscopy and consequently was identified to be 12F2P3S3M from the peak corresponding to 934 of m/z (molecular weight).

Yield amount: 1.96 g (2.09 mmol)

Yield rate: 65%

Boiling point: 172° C. to 174° C./26 Pa

Aspect: white solid

EXAMPLE 6

Measurement of physical properties is described in detail hereinafter. Physical properties are measured using glass as a substrate.

Cleaning of Glass

A slide glass (manufactured by Matsunami Glass Ind., Ltd., S-7214) was immersed into 1 N potassium hydroxide aqueous solution (pH>9) for 2 hours, then was removed and sufficiently rinsed with distilled water. Then the slide glass was dried in a desiccator and used for the following surface modification.

Preparation of Modification Solution

Silane coupling agents having various perfluoroalkyl chains were prepared to a concentration of 15 mmol/L in a solvent of iso-$C_4F_9OCH_3$ (manufactured by 3M Co., HFE-7100) and used for surface modification of glass.

Surface Modification of Glass

A slide glass, which had been cleaned by the process described above, was introduced into a 200 mL round bottom flask, which was then flushed with nitrogen gas to give a nitrogen atmosphere. Then the modification solution prepared as described above was added to the round bottom flask, and the slide glass was completely immersed into the modification solution, followed by heating and refluxing for 2 hours. After cooling, the glass was taken out and washed with a modified solvent and then distilled water. Thereafter, heat treatment was conducted in an oven at 150° C. for 30 minutes such that the remaining two methoxy groups of the silane coupling agent bonded to glass surface underwent a condensation reaction with adjacent or other methoxy groups to construct a siloxane network that forms two-or three dimensional netted siloxane bond. The glass was cooled to room temperature in a desiccator after the heat treatment to obtain modified glass.

Figure 21:
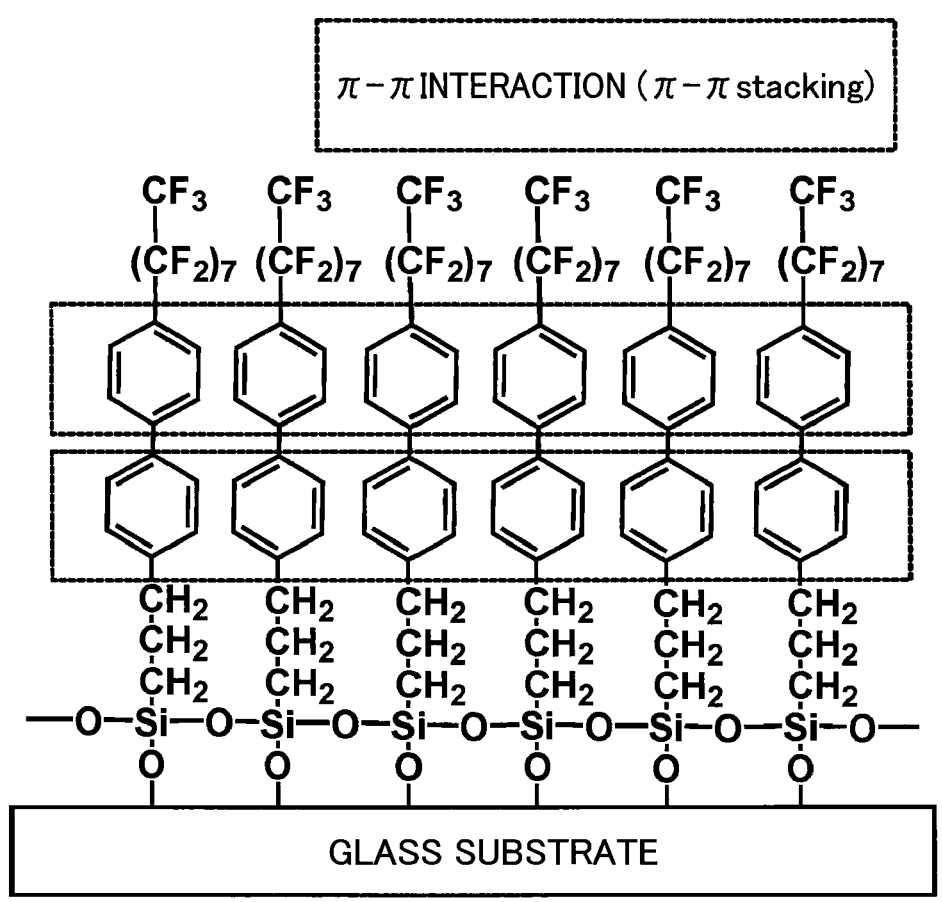
FIG. 21 is a schematic view showing a surface modified by 8F2P3S3M.

FIG. 21 shows a schematic view that represents the surface modified by 8F2P3S3M as the silane coupling agent.

Measurement of Contact Angle of Modified Glass

Contact angle of water to the modified glass was measured. In the measurement of the contact angle, a CA-X type contact angle meter (Kyowa Interface Science Co. Ltd.) was used, and a liquid drop method was employed in which a water droplet of 0.9 µL is dropped on a horizontal glass plate to measure the contact angle.

Test of Heat Resistance of Modified Glass Using 8F2P3S3M

The test results of physical properties are shown for the case using 8F2P3S3M as the silane coupling agent.

A sample of modified glass was prepared in accordance with the process described in the section of Surface Modification of Glass Described Above.

Then the modified glass was subjected to heat treatment at predetermined temperatures of 200° C., 250° C., 300° C., 350° C., 370° C., and 400° C. for 2 hours in an oven. After the heat treatment, the sample was cooled to room temperature in a desiccator and the contact angle of water to the modified glass was measured. The measurement of contact angle was performed in accordance with the process described above. The results are shown in Table 1.

TABLE 1

Table 1 8F2P3S3M

| Temperature (° C.) | Contact angle (water) |
|---|---|
| 0 | 112.0 |
| 200 | 110.0 |
| 250 | 109.0 |
| 300 | 108.0 |
| 350 | 108.0 |
| 370 | 98.0 |
| 400 | 37.0 |

Figure 22:
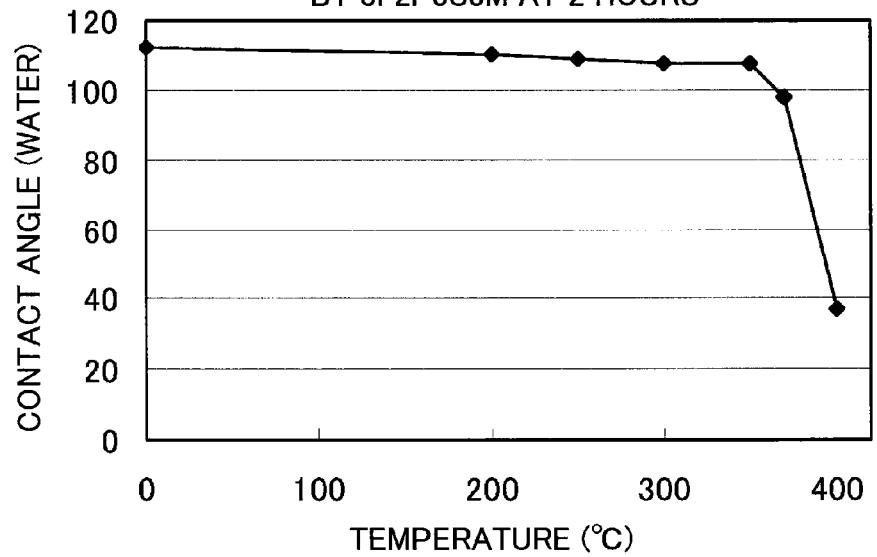
FIG. 22 is a graph showing the heat resistance of 8F2P3S3M in terms of contact angle.

The data of Table 1 are graphed and shown in FIG. 22.

The results demonstrate that the glass surface modified by the silane coupling agent of 8F2P3S3M exhibits a high contact angle even after 2 hours at 350° C.

Test of Durability of Modified Glass Using 8F2P3S3M

Similarly as above, the modified glass prepared using the 8F2P3S3M solution was tested for the change of contact angle (water) at the surface of modified glass in relation to the thermal exposure time at 350° C. to investigate heat resistance/durability. The results are shown in Table 2.

TABLE 2

Table 2 8F2P3S3M

| Time (hr) | Contact angle at 350° C. |
|---|---|
| 0 | 115.0 |
| 4 | 114.8 |
| 5 | 114.0 |
| 6 | 114.2 |
| 7 | 114.5 |
| 8 | 113.0 |

Figure 23:
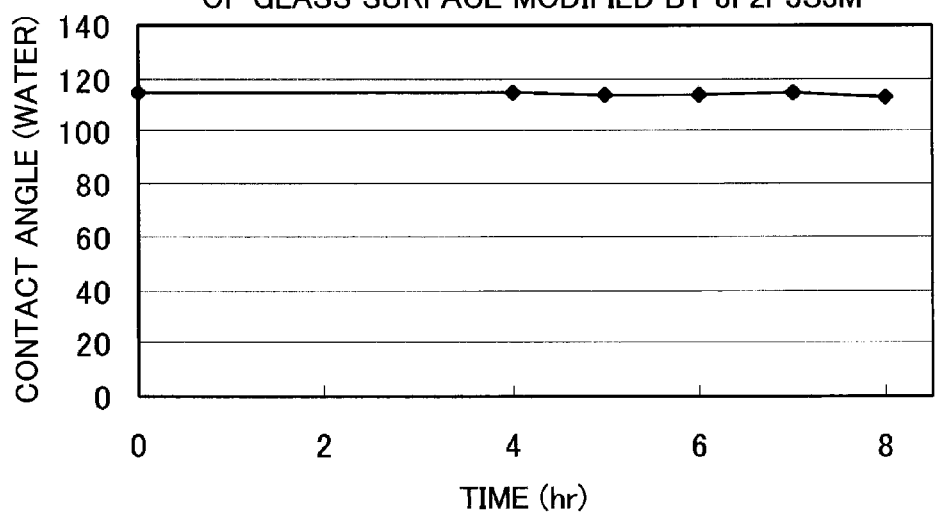
FIG. 23 is a graph showing the change of contact angle with time of 8F2P3S3M at 350° C.

The data of Table 2 are graphed and shown in FIG. 23.

The results demonstrate that the modified glass by use of the silane coupling agent of 8F2P3S3M solution maintains a high contact angle even after 8 hours at 350° C.

Heat Resistance on the Basis of Structural Difference of Silane Coupling Agents

For comparison, modified glasses by use of the modification solutions prepared using the silane coupling agents of 8F2P3S3M, 8F2P2S3M, and 8F2S3M were measured for the contact angle (water) similarly as above as to the contact angle with time in relation to the thermal exposure time at 350° C. The results are shown in Table 3.

TABLE 3

Table 3 Heat resistance on the basis of structural difference of silane coupling agents

| Time (hr) | 8F2P3S3M | 8F2P2S3M | 8F2S3M |
|---|---|---|---|
| 0 | 112 | 112 | 118 |
| 0.5 | 112 | 102 | 63 |
| 1.0 | 111 | 101.5 | 60 |
| 1.5 | 111 | 98 | 55 |
| 2.0 | 110 | 92 | 48 |

Figure 24:
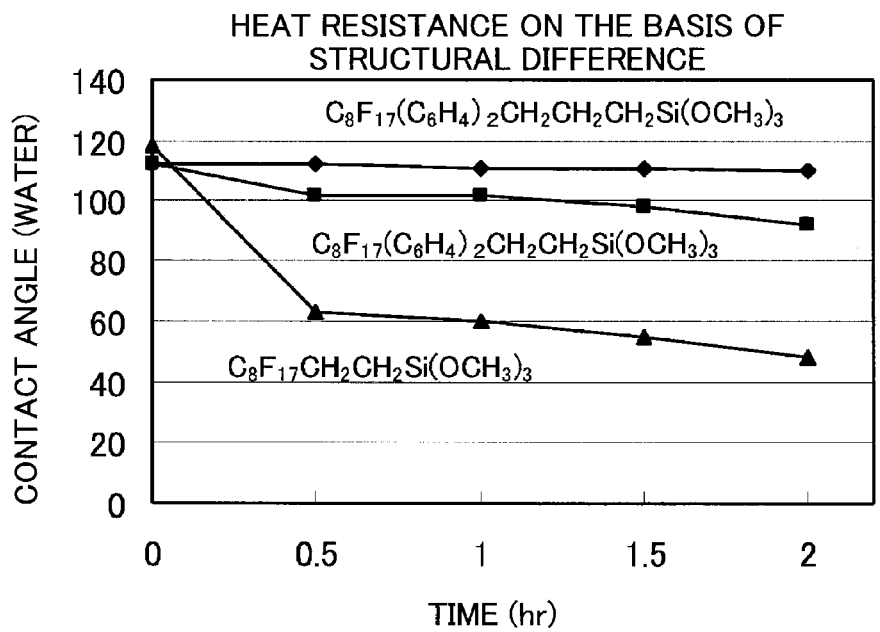
FIG. 24 is a graph comparing heat resistance on the basis of structural difference of silane coupling agents.

The data of Table 3 are graphed and shown in FIG. 24.

The results demonstrate that the silane coupling agent of 8F2P3S3M leads to higher heat resistance than 8F2P2S3M.

Heat Resistance of α-, β-isomers of 8F2P2S3M

Furthermore, the contact angle of α-, β-isomers of 8F2P2S3M was measured at identical temperatures to those used above. The results are shown in Table 4.

TABLE 4

Table 4 Contact angle of water to the glass modified by 8F2P2S3M

| Temperature (° C.) | α:β = 1:4 mixture | only α-adduct |
|---|---|---|
| 25 | 116.0 | 105.0 |
| 200 | 115.0 | 104.0 |
| 250 | 114.0 | 83.0 |
| 300 | 98.0 | 48.0 |
| 350 | 88.0 | 40.0 |

Figure 25:
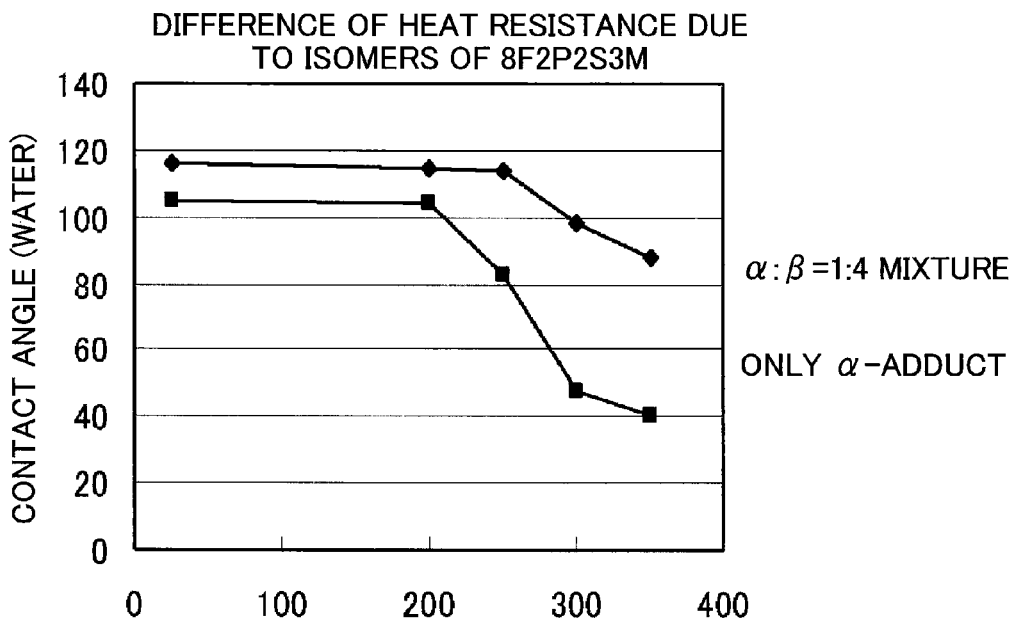
FIG. 25 is a graph showing the difference of heat resistance of 8F2P2S3M in terms of α-, β-isomers.

The data of Table 4 are graphed and shown in FIG. 25 as the difference of heat resistance of 8F2P2S3M in terms of α-, β-isomers.

Test of Heat Resistance of Modified Glass Using 10F2P3S3M

Test results of physical properties are shown for the case using 10F2P3S3M as the silane coupling agent.

A sample of modified glass was prepared in accordance with the process described in the section of Surface Modification of Glass Described Above.

Then the modified glass was subjected to heat treatment at predetermined temperatures of 250° C., 300° C., 350° C., 400° C. and 450° C. for 2 hours in an oven. After the heat treatment, the sample was cooled to room temperature in a desiccator and the contact angle of water to the modified glass was measured. The measurement of contact angle was performed in accordance with the process described above. The results are shown in Table 5 in comparison with the case using 8F2P3S3M.

TABLE 5

| Table 5 | | |
|---|---|---|
| Temperature (° C.) | 10F2P3S3M | 8F2P3S3M |
| 0 | 109.0 | 112.0 |
| 250 | 105.5 | 109.0 |
| 300 | 108.3 | 108.0 |
| 350 | 108.8 | 108.0 |
| 400 | 111.4 | 37.0 |
| 450 | 80.9 | — |

Figure 26:
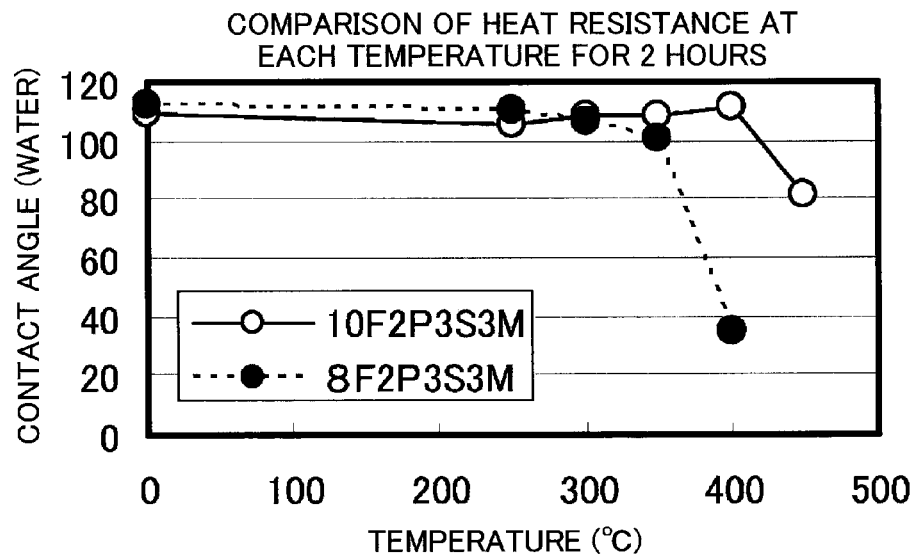
FIG. 26 is a graph comparing heat resistance of 8F2P3S3M and 10F2P3S3M in terms of contact angle.

The data of Table 5 are graphed and shown in FIG. 26. The results demonstrate that the glass surface modified by the silane coupling agent of 10F2P3S3M exhibits a high contact angle even after 2 hours at 400° C.

Test of Durability of Modified Glass Using 10F2P3S3M

Similarly as above, the modified glass prepared using the 10F2P3S3M solution was inspected for the change of contact angle (water) at the surface of modified glass in relation to the thermal exposure time at 400° C. to investigate heat resistance/durability. The results are shown in Table 6.

TABLE 6

| Table 6 10F2P3S3M | |
|---|---|
| Time (hr) | Contact angle at 400° C. |
| 0 | 119.0 |
| 2 | 111.4 |
| 4 | 107.2 |
| 6 | 107.2 |
| 8 | 112.5 |
| 10 | 110.2 |

Figure 27:
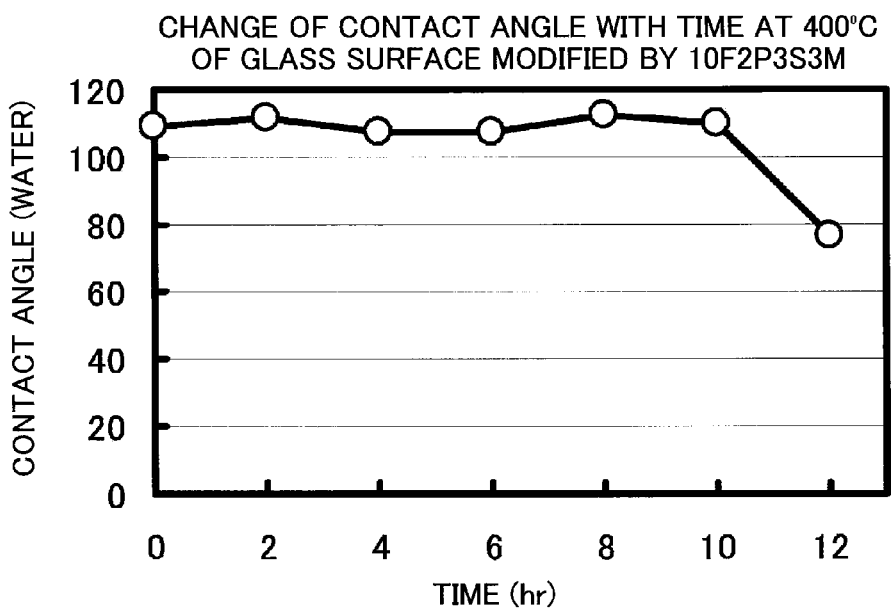
FIG. 27 is a graph showing the change of contact angle with time of 10F2P3S3M at 400° C.

The data of Table 6 are graphed and shown in FIG. 27.

The results demonstrate that the modified glass by use of the silane coupling agent of 10F2P3S3M solution exhibits a high contact angle even after 10 hours at 400° C.

The higher contact angle with water as shown by the data described above indicates the lower surface free energy and also indicates higher releasability and antifouling property.

In addition, the silane coupling agents of the present invention have higher acid resistance and oxidation resistance similarly as those of Japanese Unexamined Patent Application No. 2004-107274, although specific data are not shown.

INDUSTRIAL APPLICABILITY

As described above, the silane coupling agents having a perfluoroalkyl group and a biphenylalkyl group of the present invention are high in all of heat resistance, durability, releasability, and antifouling property and represent a monolayer (one molecular layer) of modified surface, therefore, may be not only usual mold lubricants as an excellent heat-resistant and durable mold lubricant capable of precisely mold-releasing treatment but also mold lubricants suited to metal, quartz, nickel electrocasting, and the like with micro-patterning.

They are also a most excellent mold lubricant at present as heat-resistant and durable mold lubricant for nano-imprint, the use of which is expected to expand in the immediate future.

Of course, it can be used as a highly heat resistant, water-repellent and oil-repellent surface modifier, for example, as a surface modifier of glass containers etc. that are antifouling and usable in microwave ovens.

Furthermore, any silane coupling agents can be used for surface of substrates and powders to modify their surface.

In addition, they provide a significant effect and usability as a mold lubricant or a coupling agent for heat resistant plastics, engineering plastics, etc. having a melting point of at least 300° C.

The invention claimed is:

1. A heat resistant, durable, releasable and antifouling silane coupling agent having a biphenylalkyl group, the agent being expressed by general formula (1):

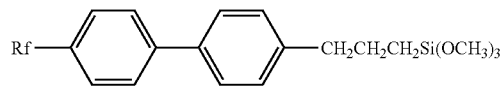

(1)

wherein in formula (1), Rf represents a perfluoroalkyl group of $F(CF_2)_n$; and wherein n is an integer of 1-14.

2. A solution for surface modification of a substrate, the solution comprising the silane coupling agent according to claim 1.

3. A coupling agent according to claim 1 selected from the group consisting of:

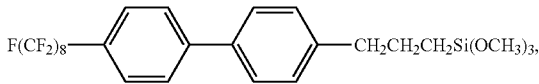

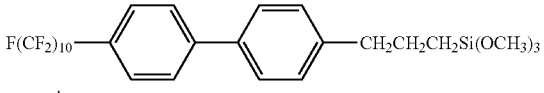

and

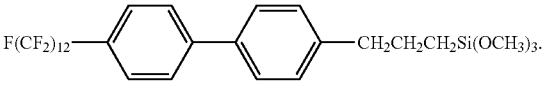

4. A purified form of a coupling agent according to claim 3.

5. A solution for surface modification of a substrate, the solution comprising the silane coupling agent according to claim 3.

6. A glass, metal, quartz, nickel electroplate or plastic having a surface modified by the silane coupling agent according to claim 1.

7. A process for producing a heat resistant, durable, releasable and antifouling silane coupling agent having a perfluoroalkyl group and a biphenylalkyl group, the process comprising:

a first synthesis step of reacting 4,4'-dibromobiphenyl expressed by general formula (2):

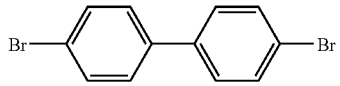 (2)

with a perfluoroalkyl iodide expressed by formula (3):

$F(CF_2)_nI$ (3)

wherein in formula (3), n is an integer of 1-14,
in a polar solvent using a catalyst of copper bronze powder to obtain 4-perfluoroalkyl-4'-bromobiphenyl expressed by general formula (4):

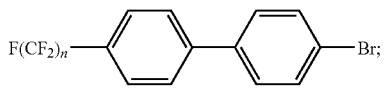 (4)

a second synthesis step of reacting the 4-perfluoroalkyl-4'-bromobiphenyl with an allyl bromide expressed by formula (5):

$CH_2=CHCH_2-Br$ (5)

in a polar solvent using a catalyst of CuI to obtain 4-perfluoroalkyl-4'-allylbiphenyl expressed by general formula (6):

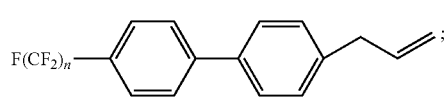 (6)

and, a third synthesis step of reacting the 4-perfluoroalkyl-4'-allylbiphenyl with trimethoxysilane expressed by formula (7):

$HSi(OCH_3)_3$ (7)

in an organic solvent using a catalyst of chloroplatinic acid to obtain (4-perfluoroalkylbiphenyl)propyltrimethoxysilane expressed by general formula (8):

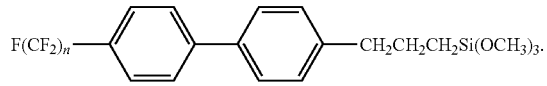 (8)

* * * * *